(12) United States Patent
Oura et al.

(10) Patent No.: US 12,303,212 B2
(45) Date of Patent: May 20, 2025

(54) ULTRASONIC DIAGNOSTIC APPARATUS, ULTRASONIC PROBE, AND ATTACHMENT FOR ULTRASONIC PROBE

(71) Applicant: Konica Minolta, Inc., Tokyo (JP)

(72) Inventors: Koji Oura, Yokohama (JP); Masahiko Kadokura, Ogaki (JP); Kaoru Okada, Hino (JP); Takashi Mizuno, Kokubunji (JP)

(73) Assignee: Konica Minolta, Inc., Tokyo (JP)

( * ) Notice: Subject to any disclaimer, the term of this patent is extended or adjusted under 35 U.S.C. 154(b) by 163 days.

(21) Appl. No.: 18/096,240

(22) Filed: Jan. 12, 2023

(65) Prior Publication Data

US 2023/0263575 A1 Aug. 24, 2023

(30) Foreign Application Priority Data

Feb. 21, 2022 (JP) ................ 2022-024794

(51) Int. Cl.
*A61B 34/20* (2016.01)
*A61B 8/00* (2006.01)
*A61B 17/34* (2006.01)
*A61B 90/00* (2016.01)

(52) U.S. Cl.
CPC ............ *A61B 34/20* (2016.02); *A61B 8/4254* (2013.01); *A61B 8/4411* (2013.01); *A61B 8/463* (2013.01); *A61B 17/3403* (2013.01); *A61B 2034/2065* (2016.02); *A61B 2090/3937* (2016.02)

(58) Field of Classification Search
CPC ..... A61B 34/20; A61B 8/4254; A61B 8/4411; A61B 8/463; A61B 17/3403; A61B 2034/2065; A61B 2090/3937; A61B 8/085; A61B 8/0891; A61B 90/13; A61B 90/37; A61B 8/4444; A61B 2034/2048;
(Continued)

(56) References Cited

U.S. PATENT DOCUMENTS

| 2017/0257619 A1* | 9/2017 | Kashima | ............ A61B 1/00188 |
| 2021/0059636 A1* | 3/2021 | Durfee | ................... A61B 8/085 |
| 2024/0033035 A1* | 2/2024 | Ootsuki | ................. A61B 17/00 |

FOREIGN PATENT DOCUMENTS

| CN | 104958095 | * 10/2015 |
| JP | 2011-505227 A | 2/2011 |
| JP | 2017-176638 A | 10/2017 |

(Continued)

*Primary Examiner* — Alexei Bykhovski
(74) *Attorney, Agent, or Firm* — RANKIN, HILL & CLARK LLP

(57) ABSTRACT

An ultrasonic diagnostic apparatus for assisting insertion of a puncture needle into a subject, includes: an ultrasonic probe that is arranged to allow a probe distal end part to be pressed against a body surface of the subject, and acquires an ultrasonic image of an inside of the subject by transmission and reception of an ultrasonic wave; an optical camera that is attached to a proximal end side of the probe and captures an image of an arrangement position of the probe distal end part of the probe on a body surface; and a laser pointer that is attached to a proximal end side of the probe and emits laser light onto a body surface to form a predetermined projection image, to guide a target insertion position and a target orientation of the needle when the needle is inserted into the subject, in an optical image acquired by the camera.

16 Claims, 17 Drawing Sheets

(58) Field of Classification Search
CPC ............ A61B 2090/378; A61B 8/0841; A61B 2017/3413; A61B 2090/365; A61B 2090/373
See application file for complete search history.

(56) References Cited

FOREIGN PATENT DOCUMENTS

| | | | |
|---|---|---|---|
| WO | WO 2004019799 | * | 3/2004 |
| WO | WO 2006038177 | * | 4/2006 |
| WO | WO 2014128301 | * | 8/2014 |

* cited by examiner

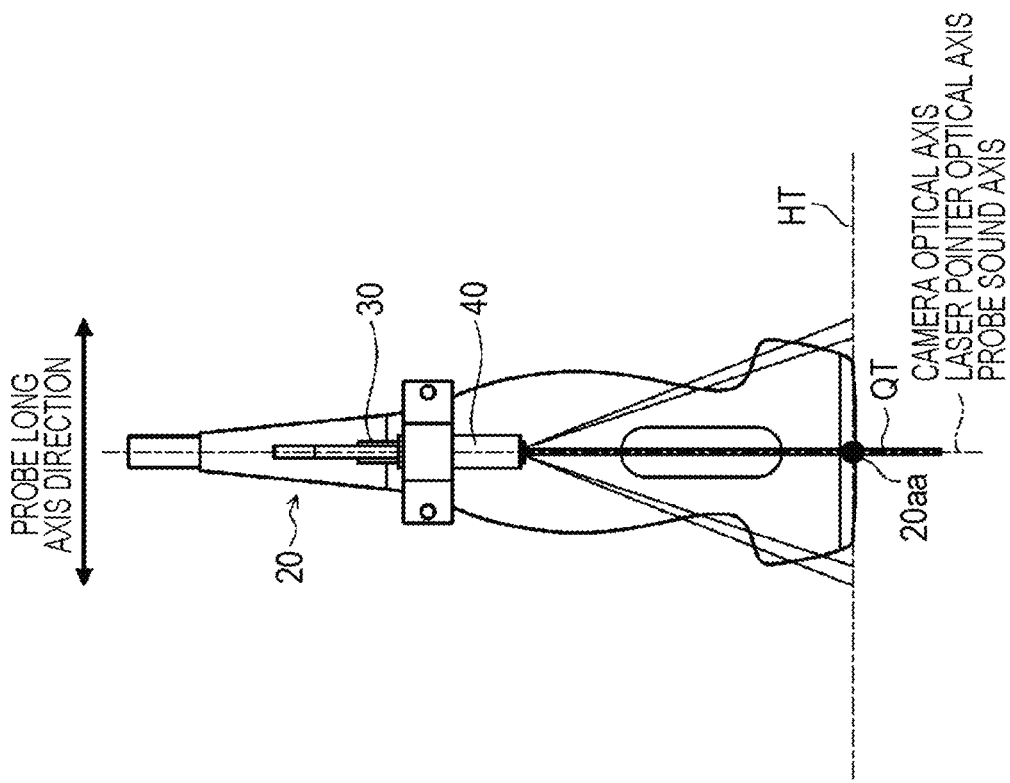
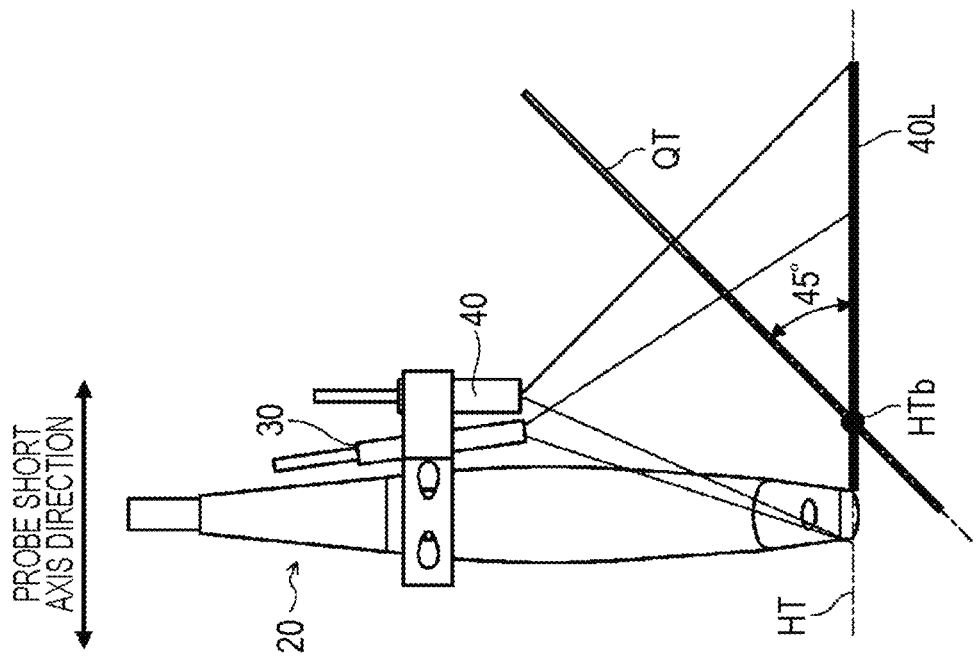

FIG. 12
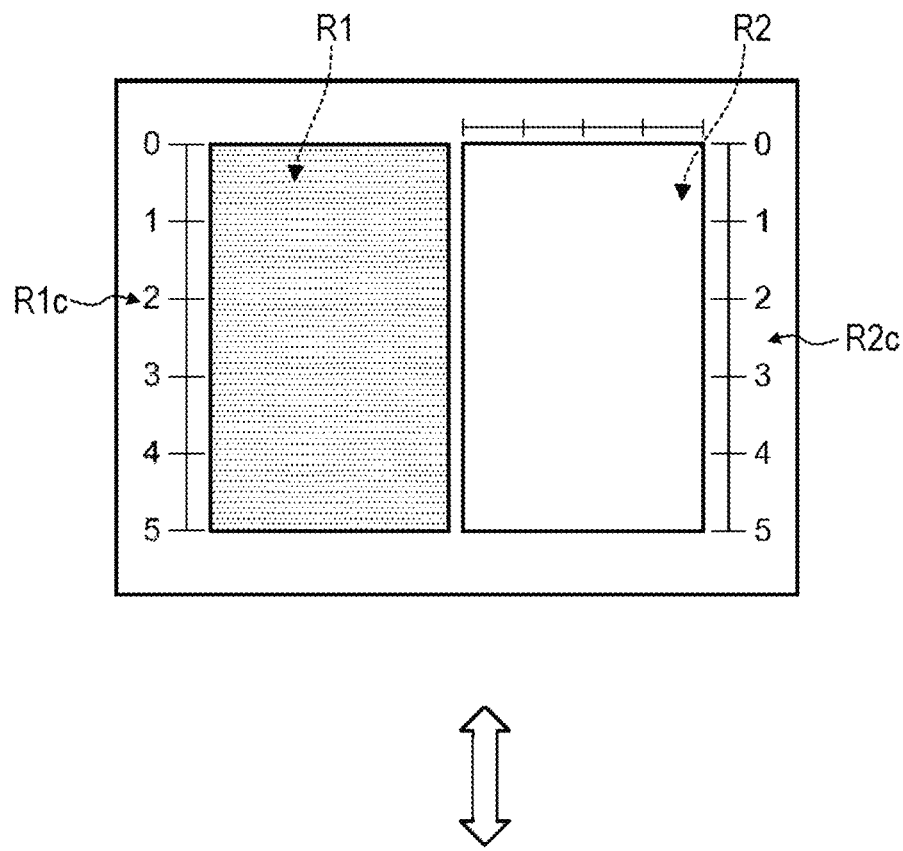
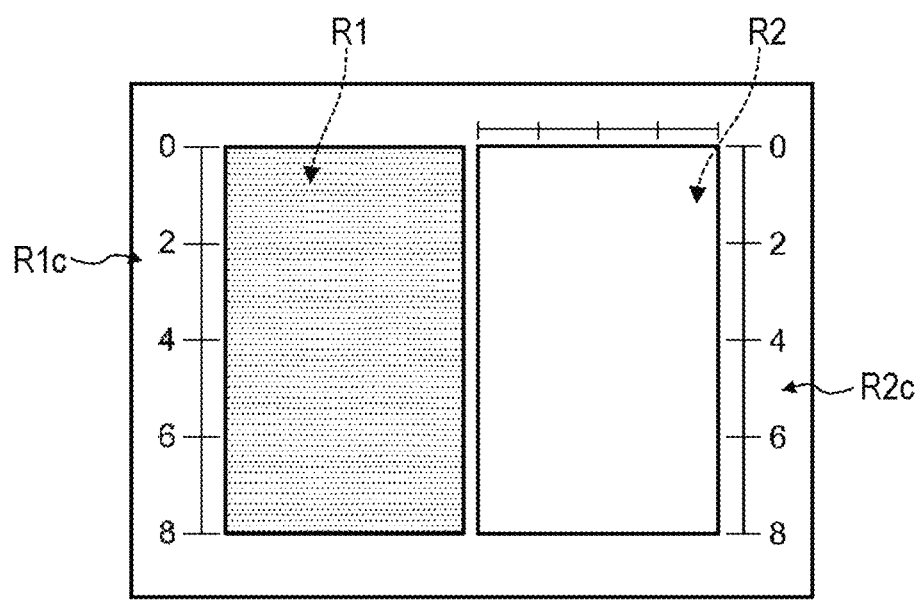

FIG. 13
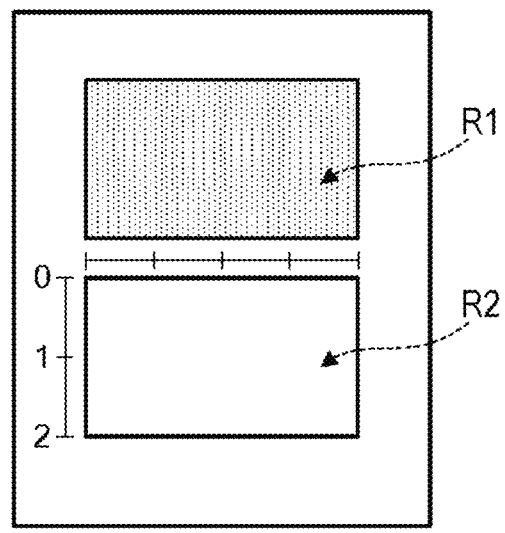
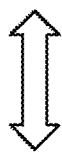
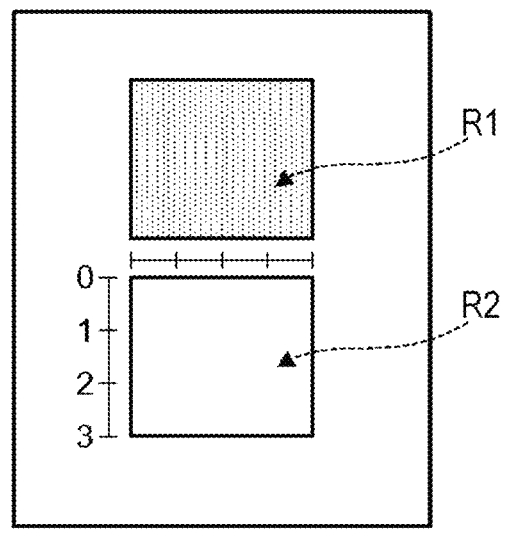

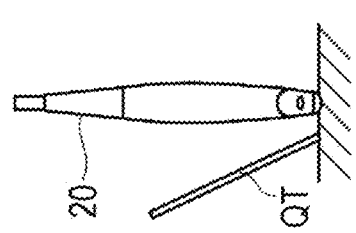
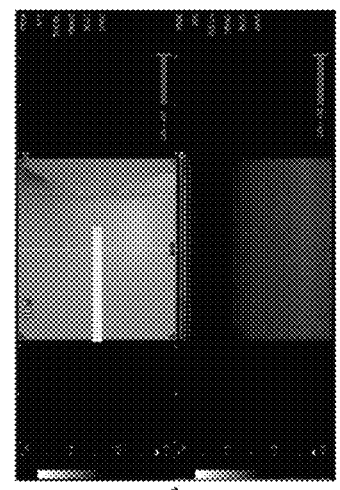
FIG. 14A
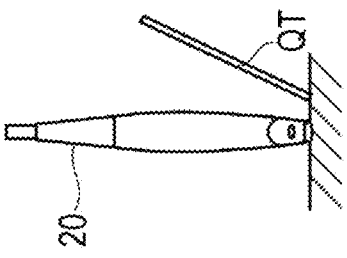
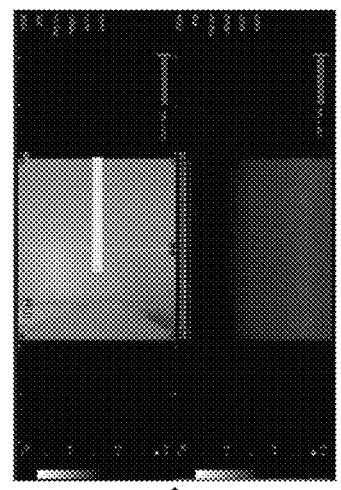
FIG. 14B
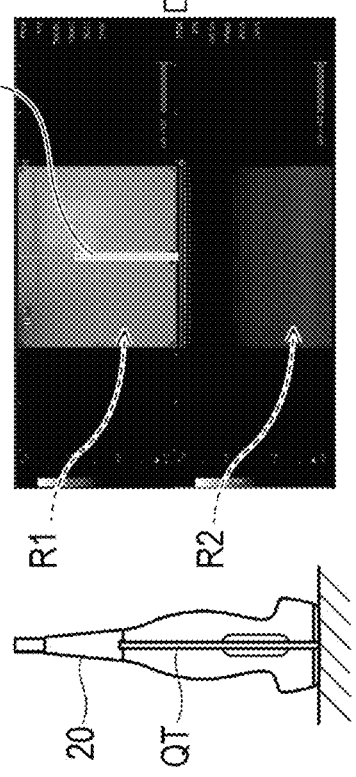
FIG. 14C
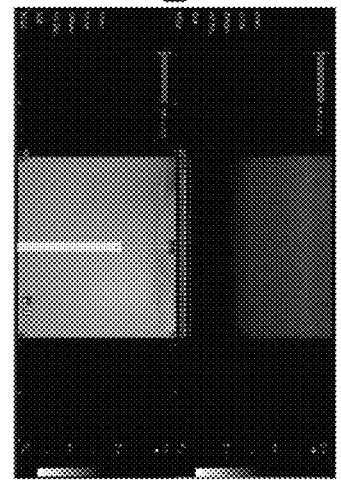
FIG. 14D

ULTRASONIC DIAGNOSTIC APPARATUS, ULTRASONIC PROBE, AND ATTACHMENT FOR ULTRASONIC PROBE

The entire disclosure of Japanese patent Application No. 2022-024794, filed on Feb. 21, 2022, is incorporated herein by reference in its entirety.

BACKGROUND

Technological Field

The present disclosure relates to an ultrasonic diagnostic apparatus, an ultrasonic probe, and an attachment for the ultrasonic probe.

Description of the Related Art

There has been known an ultrasonic diagnostic apparatus that assists insertion work of a puncture needle into a subject by capturing an internal image of the subject as an ultrasonic image. The ultrasonic diagnostic apparatus can acquire a shape, a movement, and the like of tissue in the subject as an ultrasonic image by a simple operation of applying an ultrasonic probe to a body surface of the subject.

In recent years, subject tissue diagnosis has been performed in which a puncture needle is inserted into a body of a patient as a subject, to collect tissue and body fluid. In addition, in anesthesiology, an intensive care unit, a pain clinic, and the like, treatment using a puncture needle is performed. In these diagnoses or treatments, an operator (hereinafter, referred to as a "user") such as a doctor views an ultrasonic image of subject tissue acquired by the ultrasonic diagnostic apparatus, and inserts the puncture needle into the subject while checking the subject tissue and a position of the puncture needle.

At that time, in order to reduce a burden on the patient as much as possible and perform puncture accurately, it is necessary to accurately grasp a positional relationship between an insertion position of the puncture needle on the body surface of the patient and an affected site (that is, a target) in the ultrasonic image displayed on the monitor.

In view of such a background, various techniques for assisting insertion work (hereinafter, also referred to as "puncture work") of a puncture needle into a subject have been developed in the ultrasonic diagnostic apparatus.

For example, JP 2011-505227 A discloses a needle guide to be attached to an ultrasonic probe. JP 2011-505227 A describes that the needle guide is configured so that a puncture needle can be inserted into a subject at a predetermined insertion angle, to assist insertion work of the puncture needle into the subject. In addition, JP 2011-505227 A describes that a guideline of the puncture needle guided by the needle guide is displayed on a monitor, to allow the user to recognize an entry direction of the needle.

Further, J P 2017-176638 A describes that a mark for indicating a center position (that is, a central position in a scanning direction) of an ultrasonic image is provided on a housing surface of an ultrasonic probe, and the mark enables the user to accurately recognize the central position in the scanning direction when puncturing a subject with a puncture needle.

Meanwhile, the needle guide as described in the related art according to JP 2011-505227 A is useful in terms of simplifying puncture work on a subject. However, such a needle guide has a fixed angle at which the puncture needle can be guided, so that the needle guide is unusable or conversely impairs convenience in some cases.

For example, in puncture work of a central vein such as an external jugular vein of a human (for example, puncture work for catheter insertion), in general, running of a blood vessel is confirmed by a parallel method (see a left part of FIG. 17), and puncture work of the blood vessel is performed by a cross method (see a right part of FIG. 17). At this time, since the user performs the puncture work while correcting a trajectory of the puncture needle by viewing an ultrasonic image to check an insertion state of the puncture needle into the blood vessel, manipulation is performed freehand Note that FIG. 17 illustrates a way of pressing an ultrasonic probe against a body surface of a subject in each of the parallel method (the left part of FIG. 17) and the cross method (the right part of FIG. 17), and ultrasonic images acquired at that time. In FIG. 17, reference numeral 20 denotes an ultrasonic probe, HT denotes a subject, and QT denotes a puncture needle.

In addition, in the puncture work, a target site of puncture is often present at a position deviated from a puncture guideline guided by the needle guide. In such a case, the user detaches the needle guide from the ultrasonic probe and performs the puncture work freehand.

Whereas, with the mark alone attached to the housing of the ultrasonic probe as in the related art according to JP 2017-176638 A, it is difficult to accurately grasp the positional relationship between the target site of puncture and the puncture needle. Therefore, when the puncture needle is advanced with respect to the target position (for example, a central vein) of the tissue in the subject, there is a possibility that the puncture needle is inserted from the body surface of the subject in a state of being deviated from an appropriate position or angle unless the user is skilled. As a result, the puncture needle may damage other tissue (for example, an artery, a nerve, or the like).

SUMMARY

The present disclosure has been made in view of the above problems, and an object thereof is to provide an ultrasonic diagnostic apparatus, an ultrasonic probe, and an attachment for the ultrasonic probe that can further facilitate insertion work of a puncture needle by a user into a subject.

To achieve the abovementioned object, according to an aspect of the present invention, an ultrasonic diagnostic apparatus for assisting insertion work of a puncture needle into a subject, reflecting one aspect of the present invention comprises an ultrasonic probe that is arranged to allow a probe distal end part to be pressed against a body surface of the subject, and acquires an ultrasonic image of an inside of the subject by transmission and reception of an ultrasonic wave; an optical camera that is attached to a proximal end side of the ultrasonic probe and captures an image of an arrangement position of the probe distal end part of the ultrasonic probe on a body surface of the subject; and a laser pointer that is attached to a proximal end side of the ultrasonic probe and emits laser light onto a body surface of the subject to form a predetermined projection image, to guide a target insertion position and a target orientation of the puncture needle when the puncture needle is inserted into the subject, in an optical image acquired by the optical camera.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIGS. 5A and 5B are views illustrating a positional relationship between the puncture needle and an image-capturing region of the optical camera and a positional relationship between the puncture needle and a projection image of laser light of the laser pointer at a time of puncture work;

FIG. 12 is a view illustrating an example of a configuration of an ultrasonic diagnostic apparatus according to Modification 4;

FIG. 13 is a view illustrating an example of a configuration of an ultrasonic diagnostic apparatus according to Modification 5;

FIGS. 14A to 14D are views illustrating an example of a configuration of an ultrasonic diagnostic apparatus according to Modification 6;

DETAILED DESCRIPTION OF EMBODIMENTS

Figure 1:
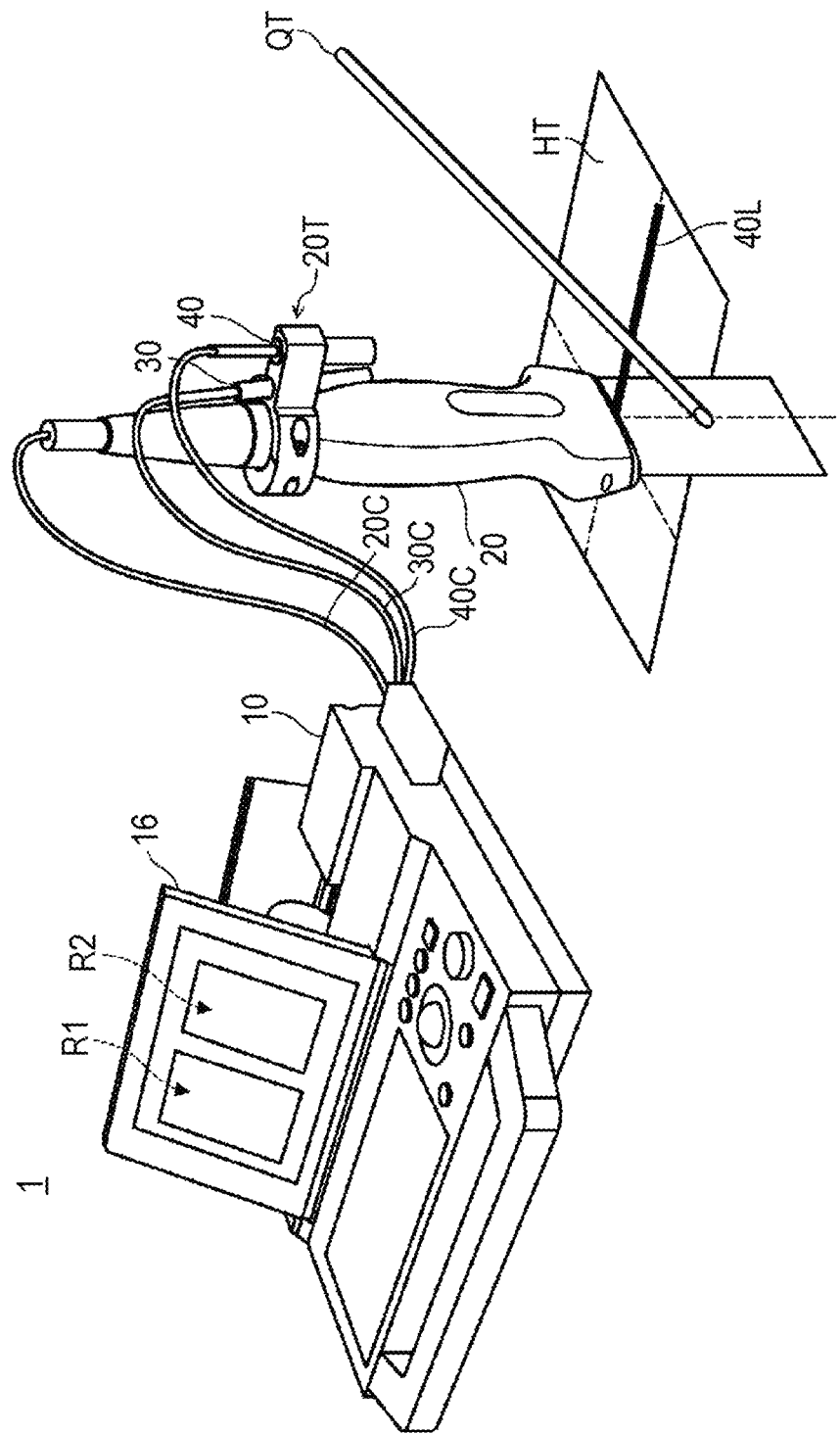
FIG. 1 is a view illustrating an overall configuration of an ultrasonic diagnostic apparatus according to an embodiment of the present invention.

Hereinafter, one or more embodiments of the present invention will be described with reference to the drawings. However, the scope of the invention is not limited to the disclosed embodiments. Note that, in the present specification and the drawings, components having substantially the same function are denoted by the same reference numerals, and redundant description is omitted.

[Overall Configuration of Ultrasonic Diagnostic Apparatus]

First, with reference to FIGS. 1 and 2, an overall configuration of an ultrasonic diagnostic apparatus (hereinafter, referred to as an "ultrasonic diagnostic apparatus 1") according to an embodiment of the present invention will be described.

Figure 2:
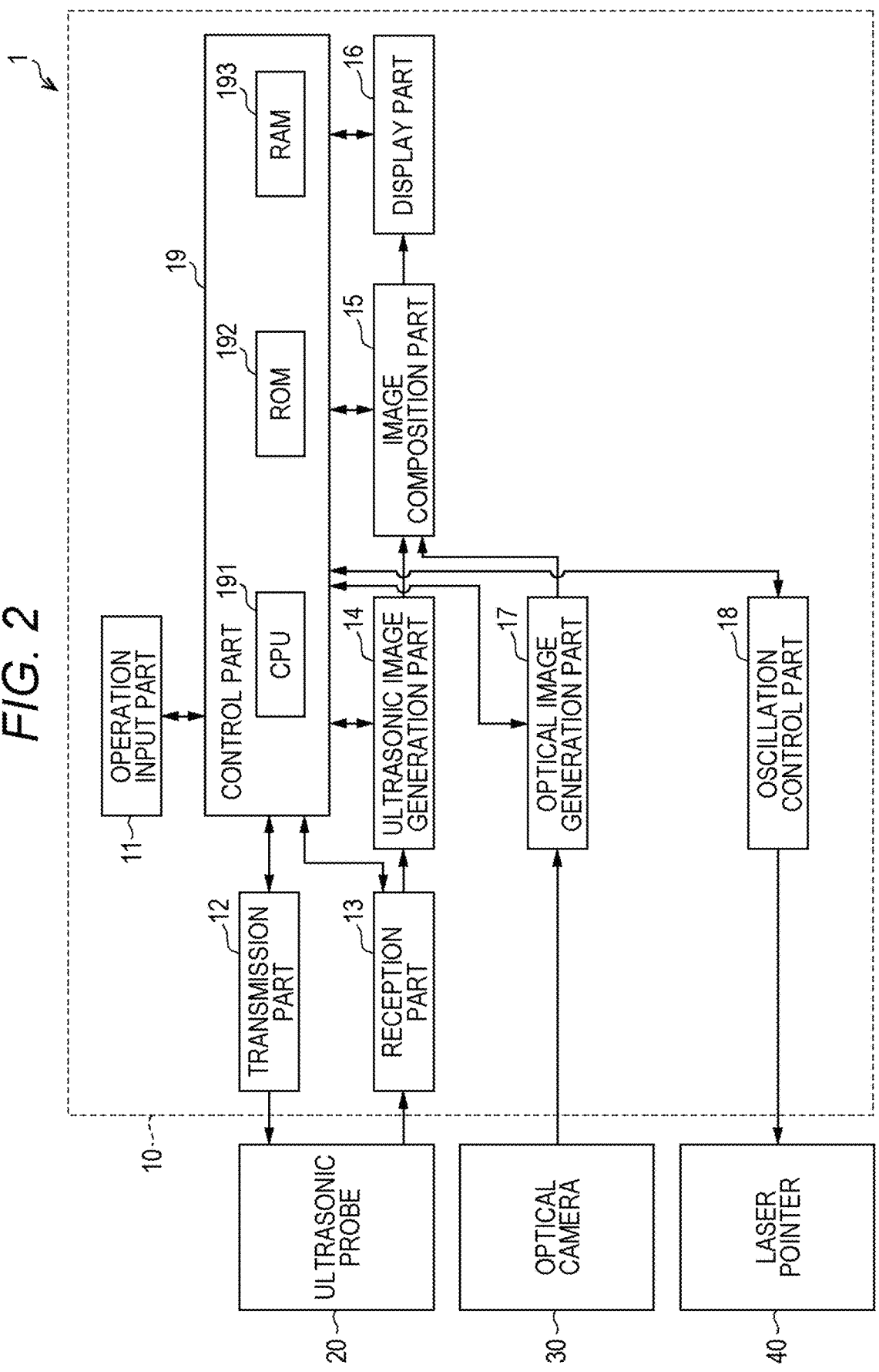
FIG. 2 is a diagram illustrating functional blocks of an ultrasonic diagnostic apparatus main body according to an embodiment of the present invention.

FIG. 1 is a view illustrating an overall configuration of the ultrasonic diagnostic apparatus 1 according to the present embodiment. FIG. 2 is a view illustrating functional blocks of an ultrasonic diagnostic apparatus main body 10 according to the present embodiment.

Figure 3B:
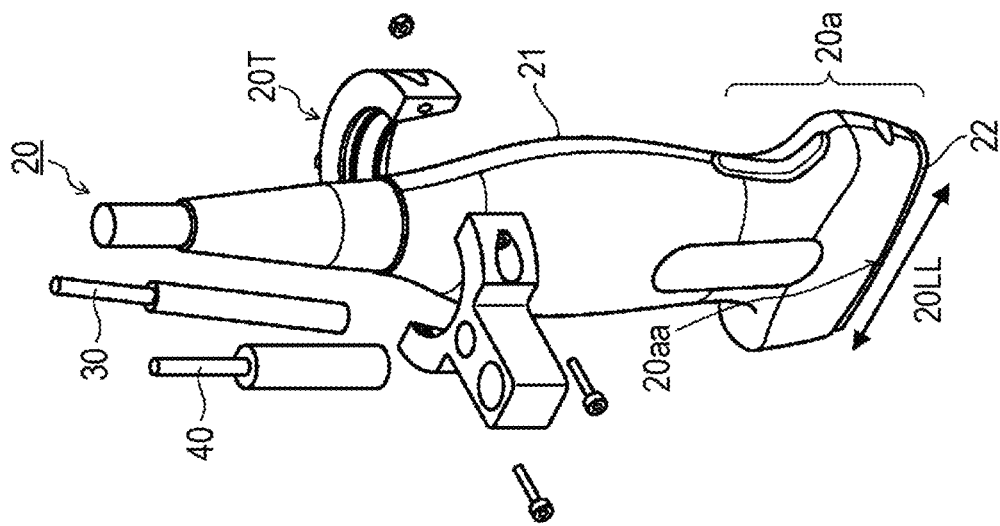
FIGS. 3A and 3B are views illustrating a configuration of an ultrasonic probe according to an embodiment of the present invention.
Figure 3A:
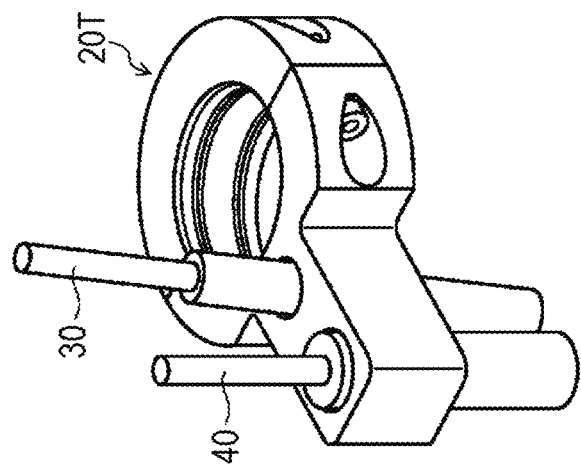

FIGS. 3A and 3B are views illustrating a configuration of an ultrasonic probe 20 according to the present embodiment. Note that FIG. 3A illustrates a configuration of an attachment 20T to be attached to the ultrasonic probe 20, and FIG. 3B illustrates an example of an attachment state of the attachment 20T to the ultrasonic probe 20.

The ultrasonic diagnostic apparatus 1 includes the ultrasonic diagnostic apparatus main body 10, the ultrasonic probe 20, an optical camera 30, and a laser pointer 40. The ultrasonic probe 20, the optical camera 30, and the laser pointer 40 are connected to the ultrasonic diagnostic apparatus main body 10 via cables 20C, 30C, and 40C, respectively.

In puncture work using the ultrasonic diagnostic apparatus 1 according to the present embodiment, for example, it is assumed that a puncture needle QT is inserted into a subject HT freehand by a user. The user brings a transmission/reception surface for an ultrasonic beam in the ultrasonic probe 20 into contact with a body surface of the subject HT and operates the ultrasonic diagnostic apparatus 1, to obtain an ultrasonic image of an inside of the subject HT. Then, while checking a target position in the subject HT shown in an ultrasonic image R1 by viewing a display part 16, the user grasps a target insertion position and a target orientation of the puncture needle QT when the puncture needle QT is inserted into the subject HT from an optical image R2 acquired by the optical camera 30, and performs the puncture work. At this time, in the optical image R2 acquired by the optical camera 30, the target insertion position and the target orientation of the puncture needle QT are shown by a projection image 40L formed on the body surface of the subject by laser light emitted from the laser pointer 40, which allows the user to perform accurate puncture work (to be described later with reference to FIGS. 7 and 8).

The ultrasonic probe 20 functions as an acoustic sensor that transmits an ultrasonic beam (for example, about 1 to 30 MHz) into the subject HT (for example, a human body), and receives an ultrasonic echo reflected in the subject HT among the transmitted ultrasonic beams and converts the ultrasonic echo into an electric signal. Note that, in the present embodiment, a linear probe is shown as an example of the ultrasonic probe 20, but any probe such as a convex probe, a sector probe, or a three-dimensional probe can be applied as the ultrasonic probe 20.

The ultrasonic probe 20 includes, for example, a housing 21 and a transducer array 22 disposed at a probe distal end part 20a of the housing 21 (see FIG. 3B).

The housing 21 has an elongated shape, for example, and also serves as a grip portion to be gripped by the user. To the housing 21, the attachment 20T is attached to a proximal end side, and the optical camera 30 and the laser pointer 40 are fixed to the housing 21 via the attachment 20T.

The transducer array 22 is disposed so as to form an ultrasonic transmission/reception surface at the probe distal end part 20a of the housing 21. The transducer array 22 includes a plurality of transducers (for example, a piezoelectric elements) arranged along a long axis direction (a direction of 20LL in FIG. 3B) of the probe distal end part 20a of the housing 21. Note that, at a time of acquiring an ultrasonic image, ultrasonic scanning in the subject HT is performed along the long axis direction of the probe distal end part 20a by sequentially switching ON and OFF of a drive state of each transducer of the transducer array 22. Then, an ultrasonic image is generated representing a two-dimensional structure within a cross section including a transmission direction of an ultrasonic wave (that is, a depth direction of the subject HT) and a scanning direction of the ultrasonic wave (that is, the long axis direction of the probe distal end part 20a).

The ultrasonic diagnostic apparatus main body 10 includes an operation input part 11, a transmission part 12, a reception part 13, an ultrasonic image generation part 14, an image composition part 15, the display part 16, an optical image generation part 17, an oscillation control part 18, and a control part 19.

The operation input part 11 receives, for example, a command instructing start of diagnosis or the like or an input of information regarding the subject HT. The operation input part 11 includes, for example, an operation panel having a plurality of input switches, a keyboard, a mouse, and the like. Note that the operation input part 11 may include a touch panel provided integrally with the display part 16.

The transmission part 12 is a transmitter that transmits a voltage pulse as a drive signal to the ultrasonic probe 20, in accordance with an instruction from the control part 19. The transmission part 12 includes, for example, a high-frequency pulse oscillator, a pulse setting part, and the like. The transmission part 12 adjusts a voltage pulse generated by the high-frequency pulse oscillator to a voltage amplitude, a pulse width, and a transmission timing set by the pulse setting part, and transmits the voltage pulse for each channel of the ultrasonic probe 20.

The transmission part 12 includes a pulse setting part in each of the plurality of channels of the ultrasonic probe 20, and can set a voltage amplitude, a pulse width, and a transmission timing of the voltage pulse for each of the plurality of channels. For example, the transmission part 12 changes a target depth or generates a different pulse waveform by setting an appropriate delay time for the plurality of channels.

The reception part 13 is a receiver that performs reception processing on a reception signal related to an ultrasonic echo generated by the ultrasonic probe 20, in accordance with an instruction of the control part 19. The reception part 13 includes a pre-amplifier, an AD conversion part, and a reception beamformer.

The reception part 13 amplifies a reception signal related to a weak ultrasonic echo for each channel by the pre-amplifier, and converts the reception signal into a digital signal by the AD conversion part. Then, the reception part 13 collects the reception signals of the plurality of channels into one by phasing addition of the reception signals of the individual channels by the reception beamformer, to obtain acoustic beam data.

The ultrasonic image generation part 14 acquires a reception signal (acoustic line data) from the reception part 13, and generates an ultrasonic image (that is, a tomographic image) of the inside of the subject HT.

For example, when the ultrasonic probe 20 transmits a pulsed ultrasonic beam in a depth direction, the ultrasonic image generation part 14 accumulates a signal intensity of an ultrasonic echo detected thereafter in a line memory temporally continuously. Then, the ultrasonic image generation part 14 sequentially accumulates the signal intensity of the ultrasonic echo at each scanning position into the line memory to generate two-dimensional data in units of frames, in response to the ultrasonic beam from the ultrasonic probe 20 scanning the inside of the subject HT. Then, by converting the signal intensity of the two-dimensional data into a luminance value, the ultrasonic image generation part 14 generates an ultrasonic image representing a two-dimensional structure in a cross section including the transmission direction of the ultrasonic wave and the scanning direction of the ultrasonic wave.

The image composition part 15 acquires data of an ultrasonic image from the ultrasonic image generation part 14, and acquires data of an optical image from the optical image generation part 17. Then, the image composition part 15 generates a display image that displays the ultrasonic image and the optical image in the same display screen (see FIG. 6). Then, the image composition part 15 sends data of the generated display image, to the display part 16. Every time data of a new ultrasonic image is acquired from the ultrasonic image generation part 14 and/or every time data of a new optical image is acquired from the optical image generation part 17, the image composition part 15 updates the display image in real time, and causes the display part 16 to display the display image in a moving image format.

Note that the image composition part 15 may be able to change a display mode of the ultrasonic image and/or the optical image in the display image in accordance with an instruction of the control part 19 (or setting contents inputted to the operation input part 11).

Furthermore, the image composition part 15 may generate a display image after performing predetermined image processing on the ultrasonic image outputted from the ultrasonic image generation part 14 or the optical image outputted from the optical image generation part 17.

The display part 16 includes, for example, a liquid crystal display, an organic EL display, a CRT display, or the like. In accordance with an instruction from the control part 19, the display part 16 acquires data of a display image from the image composition part 15, and displays the display image.

The optical image generation part 17 acquires an image signal from the optical camera 30, and generates image data related to the optical image. For example, the optical image generation part 17 continuously generates optical image data in units of frames on the basis of image signals sequentially obtained from the optical camera 30, and generates optical image data in a moving image format.

Note that the optical image generation part 17 may be incorporated in the optical camera 30.

The oscillation control part 18 controls a driving current flowing through a laser diode of the laser pointer 40, and controls ON/OFF of an operation of the laser pointer 40. Note that the oscillation control part 18 operates in accordance with an instruction from the control part 19.

Note that the transmission part 12, the reception part 13, the ultrasonic image generation part 14, the image composition part 15, the optical image generation part 17, and the oscillation control part 18 include, for example, dedicated or general-purpose hardware (electronic circuit) corresponding to each process, such as a digital signal processor (DSP), an application specific integrated circuit (ASIC), or a programmable logic device (PLD), and realizes each function in cooperation with the control part 19.

The control part 19 performs overall control of the ultrasonic diagnostic apparatus 1 by controlling the operation input part 11, the transmission part 12, the reception part 13, the ultrasonic image generation part 14, the image composition part 15, the display part 16, the optical image generation part 17, and the oscillation control part 18 in accordance with the individual functions.

The control part 19 includes a central processing unit (CPU) 191 as an arithmetic/control device, a read only memory (ROM) 192 and a random access memory (RAM) 193 as a main storage device, and the like. The ROM 192 stores a basic program and basic setting data. The CPU 191 reads a program corresponding to a processing content from the ROM 192, develops the program in the RAM 193, and executes the developed program, to centrally control operations of individual functional blocks (the operation input part 11, the transmission part 12, the reception part 13, the ultrasonic image generation part 14, the image composition part 15, the display part 16, the optical image generation part 17, and the oscillation control part 18) of the ultrasonic diagnostic apparatus main body 10.

[Detailed Configuration of Optical Camera 30 and Laser Pointer 40]

Figure 4:
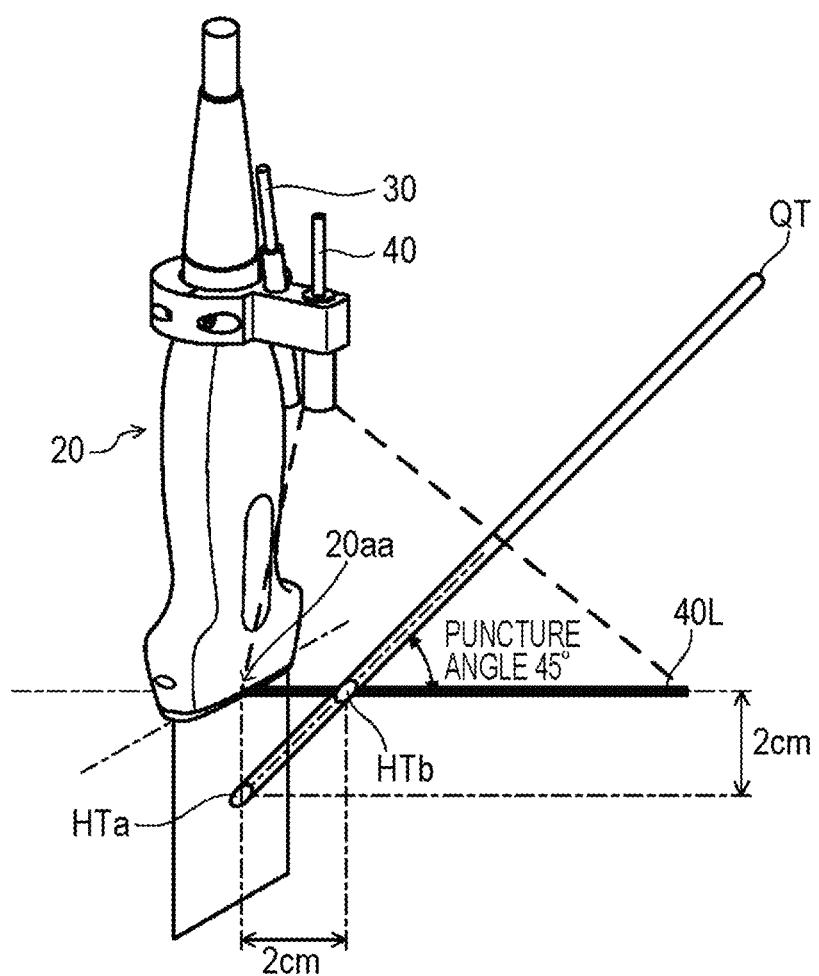
FIG. 4 is a view illustrating a positional relationship between a puncture needle and an image-capturing region of an optical camera and a positional relationship between the puncture needle and a projection image of laser light of a laser pointer at a time of puncture work.

FIGS. 4, 5A, and 5B are views illustrating a positional relationship between the puncture needle QT and an image-capturing region of the optical camera 30 and a positional relationship between the puncture needle QT and the projection image 40L of laser light of the laser pointer 40, at a time of the puncture work.

FIG. 4 is a perspective view of the ultrasonic probe 20 as viewed obliquely from above, FIG. 5A is a side view of the ultrasonic probe 20 (which means a view of a short axis side of the ultrasonic probe 20, the same applies hereinafter), and FIG. 5B is a front view of the ultrasonic probe 20 (which means a view of a long axis side of the ultrasonic probe 20, the same applies hereinafter).

Figure 6:
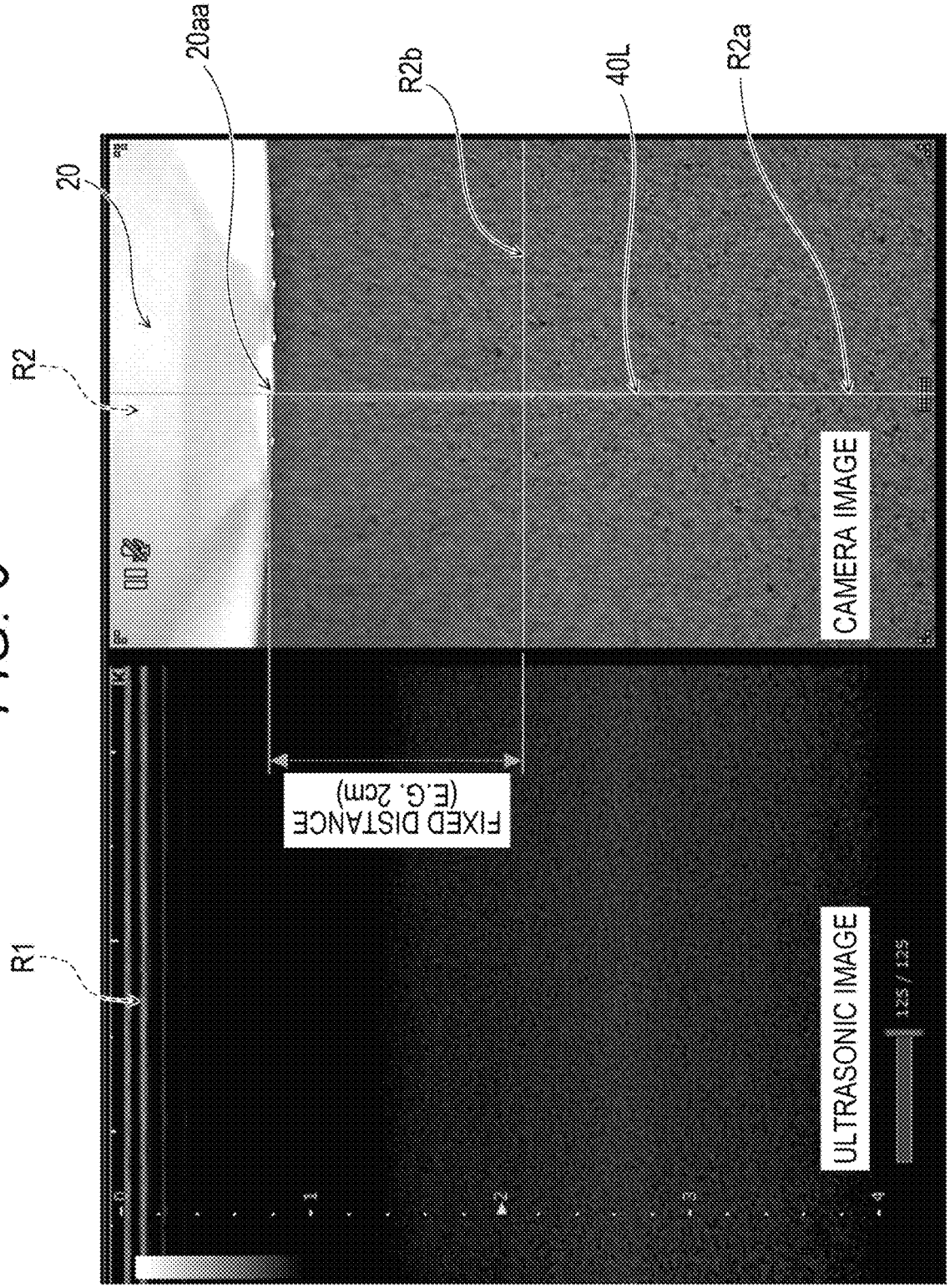
FIG. 6 is a view illustrating an example of a monitor screen displayed on a display part of the ultrasonic diagnostic apparatus in a guide mode activated at a time of puncture work.

FIG. 6 is a view illustrating an example of a monitor screen displayed on the display part 16 of the ultrasonic diagnostic apparatus 1 in a guide mode (hereinafter, referred to as a "puncture work guide mode") activated at a time of puncture work. In FIG. 6, an ultrasonic image acquired by the ultrasonic probe 20 is displayed in a left region R1 of the monitor screen, and an optical image acquired by the optical camera 30 is displayed in a right region R2 of the monitor screen.

The optical camera 30 is, for example, a general visible camera that acquires an optical image by a built-in imaging element. The optical camera 30 includes, for example, a zoom lens, and is capable of enlarging and imaging an image-capturing target (here, a body surface region of the subject HT).

The optical camera 30 is attached to a proximal end side of the ultrasonic probe 20, and captures an image of an arrangement position of the probe distal end part 20a of the ultrasonic probe 20 on a body surface of the subject HT. The optical camera 30 is attached to the ultrasonic probe 20 to show, in the optical image R2, the probe distal end part 20a of the ultrasonic probe 20, the projection image 40L formed by projecting the laser light from the laser pointer 40 onto the body surface of the subject HT, and an observation target site of the ultrasonic image R1 on the body surface of the subject HT.

This allows the user to recognize, from the optical image R2, a relative positional relationship between the probe distal end part 20a of the ultrasonic probe 20 on the body surface of the subject HT and an ultrasonic scan cross section (that is, a tomographic plane of the ultrasonic image), and a target insertion position and a target orientation of the puncture needle QT on the body surface of the subject HT at a time of the puncture work (described later with reference to FIG. 6).

Note that an image signal generated by the imaging element built in the optical camera 30 is transmitted to the ultrasonic diagnostic apparatus main body 10, subjected to AD conversion processing or the like in the optical image generation part 17 of the ultrasonic diagnostic apparatus main body 10, and converted into image data of an optical image.

The laser pointer 40 is, for example, a general semiconductor laser that outputs laser light of visible color (for example, red laser light having a wavelength of 635 nm to 690 nm). The laser pointer 40 is attached to a proximal end side of the ultrasonic probe 20, and emits the laser light onto the body surface of the subject HT to form the predetermined projection image 40L, to guide the target insertion position and the target orientation of the puncture needle QT when the puncture needle QT is inserted into the subject HT, in the optical image R2 acquired by the optical camera 30.

The laser pointer 40 according to the present embodiment outputs the laser light such that a shape (that is, an irradiation shape) of the projection image 40L of the laser light on the body surface of the subject HT becomes linear by its own built-in diffraction grating or slit. Note that ON/OFF control of the operation of the laser pointer is performed by the oscillation control part 18 of the ultrasonic diagnostic apparatus main body 10.

The projection image 40L formed by the laser light of the laser pointer 40 guides the target insertion position and the target orientation of the puncture needle QT with the probe distal end part 20a of the ultrasonic probe 20 as a reference position, in the optical image R2 acquired by the optical camera 30. For example, by using, as a starting point, a central position 20aa (hereinafter, also referred to as a "sound axis center") in a long axis direction (the direction of 20LL illustrated in FIG. 3B) of the probe distal end part 20a of the ultrasonic probe 20, on the body surface of the subject HT, the projection image 40L formed by the laser light of the laser pointer 40 presents a linear shape extending from the starting point toward a direction orthogonal to the long axis direction (that is, a direction away from the probe distal end part 20a).

This allows the user to recognize the central position 20aa of the probe distal end part 20a of the ultrasonic probe 20 in the long axis direction and the direction orthogonal to the long axis direction on the body surface of the subject HT. That is, in this way, by using a position of the probe distal end part 20a of the ultrasonic probe 20 arranged on the body surface of the subject HT as a reference, it is possible to guide, to the user, a position of a target site (for example, a blood vessel to be punctured) shown in the ultrasonic image R1, and further, the target orientation and the target insertion position of the puncture needle QT when the puncture needle QT is inserted into the subject HT. Note that the target orientation of the puncture needle QT means, for example, an appropriate orientation of the puncture needle QT in plan view (which means a visual field from above the body surface of the subject HT, the same applies hereinafter).

In FIGS. 4, 5A, and 5B, HTa represents a target site in the subject HT, and HTb represents a target insertion position when the puncture needle QT is inserted into the subject HT. Here, an extending direction of the linear projection image 40L of the laser light is to be the target orientation of the puncture needle QT when the puncture needle QT is inserted into the subject HT.

Further, at this time, the target insertion position HTb of the puncture needle QT is set, for example, in a state where an angle of the puncture needle QT in plan view is adjusted to the target orientation and an elevation angle of the puncture needle QT with respect to the body surface of the subject HT is adjusted to 45°. That is, as illustrated in FIG. 4, when the target site HTa is present at a position of 2 cm from the body surface of the subject HT, the target insertion position HTb of the puncture needle QT is set at a position separated by 2 cm along the projection image 40L of the laser light from the central position 20aa in the long axis direction of the probe distal end part 20a. However, the elevation angle of the puncture needle QT with respect to the body surface of the subject HT may be other than 45°. In this case, the target insertion position HTb of the puncture needle QT may simply be set according to the elevation angle of the puncture needle QT.

Note that, when the puncture work is performed under an ultrasonic guide, typically, first, the ultrasonic probe 20 is subjected to a moving operation by the user on the body surface of the subject HT such that the target site (that is, a puncture target site) HTa in the subject HT is located at a center position (that is, the central position 20aa in the long axis direction of the probe distal end part 20a of the ultrasonic probe 20) in the scanning direction of the ultrasonic image R1.

The camera 30 and the laser pointer 40 are set such that a sound axis center of the ultrasonic probe 20, an optical axis of the camera 30, and an optical axis of the laser pointer 40 coincide with each other in front view (see FIG. 5B). In other words, the optical axis of the optical camera 30 and the sound axis center of the ultrasonic probe are individually set so as to overlap with the center axis of the projection image 40L of the laser light outputted from the laser pointer 40 when the projection image 40L is projected onto the body surface of the subject HT. As a result, the projection image 40L of the laser light projected on the body surface of the subject HT indicates a direction orthogonal to the long axis direction with, as a starting point, the central position 20aa in the long axis direction of the probe distal end part 20a of the ultrasonic probe 20. That is, the user can recognize the target orientation and the target insertion position of the puncture needle QT by viewing the projection image 40L of the laser light reflected in the optical image R2.

Note that, in the ultrasonic diagnostic apparatus 1 according to the present embodiment, the camera 30 and the laser pointer 40 are attached to the housing 21 of the ultrasonic probe 20 via the detachable attachment 20T (see FIGS. 3A and 3B) so as to have a predetermined positional relationship with respect to the ultrasonic probe 20 as described above. Then, the positional relationship of the camera 30 and the laser pointer 40 with respect to the ultrasonic probe 20 is positioned by the attachment 20T. However, the attachment 20T may be capable of adjusting orientations of the optical camera 30 and the laser pointer 40.

The attachment 20T is, for example, a screw-fastening sandwiching member, and is attached to the housing 21 so as to sandwich the housing 21 of the ultrasonic probe 20 from both left and right sides. The attachment 20T is made by, for example, a material that can withstand disinfectants, for example, polyacetal (POM). Further, when the attachment 20T is attached to the ultrasonic probe 20, in order to establish a state where the ultrasonic probe 20, the camera 30, and the laser pointer 40 are aligned, for example, a probe notch (not illustrated) is provided on an outer surface of the housing 21 of the ultrasonic probe 20, and a protrusion (not illustrated) to be fitted into the probe notch is provided on an inner peripheral surface of the attachment 20T.

Next, the puncture work by the user when the puncture needle QT is inserted into the body surface of the subject HT by using the ultrasonic diagnostic apparatus 1 according to the present embodiment will be described.

The puncture work by the user is performed in a state where the puncture work guide mode is activated in the ultrasonic diagnostic apparatus 1, and the ultrasonic image R1 acquired by the ultrasonic probe 20 and the optical image R2 (that is, the optical image R2 in which the body surface of the observation target site of the subject HT is enlarged) acquired by the optical camera 30 are displayed in the same screen of the display part 16 (that is, in the display image).

For example, as illustrated in FIG. 6, the image composition part 15 generates a display image in which the ultrasonic image R1 acquired by the ultrasonic probe 20 and the optical image R2 acquired by the optical camera are arranged side by side.

Furthermore, at this time, the image composition part 15 superimposes and displays, in the optical image R2 of the display image, a vertical imaginary line R2a indicating a line of an optical axis of the optical camera 30 and a horizontal imaginary line R2b indicating a line orthogonal to an optical axis of the optical camera 30, for example, as illustrated in FIG. 6. The vertical imaginary line R2a and the horizontal imaginary line R2b have a role of supporting the function of guiding the target orientation and the target insertion position of the puncture needle QT in the projection image 40L formed by the laser light.

Specifically, the vertical imaginary line R2a functions to allow the user to recognize the long-axis direction central position 20aa of the probe distal end part 20a and an angular deviation when the puncture needle QT is inserted. In addition, the horizontal imaginary line R2b functions to allow the user to recognize a distance of the insertion position of the puncture needle QT from the probe distal end part 20a. FIG. 6 illustrates an aspect in which one horizontal imaginary line R2b is displayed at a position of 2 cm from the probe distal end part 20a. Note that a distance (in FIG. 6, the position of 2 cm) from the probe distal end part 20a in the optical image R2 is specified in advance from a holding state of the camera 30 in the attachment 20T.

Note that a display position, the number of pieces, a display interval, and the like of the horizontal imaginary line R2b may be appropriately changed, for example, on the basis of an orientation of the ultrasonic probe 20, a display scale of the ultrasonic image R1 and/or the optical image R2, or user setting (see FIGS. 10, 12, 13, and 14A to 14D described later).

Furthermore, the optical image R2 may be provided with a scale for allowing recognition of a correspondence between a distance in the optical image R2 and an actual distance, or a correspondence between a distance in the optical image R2 and a distance in the ultrasonic image R1 (see FIGS. 12 and 13 to be described later).

Figure 7:
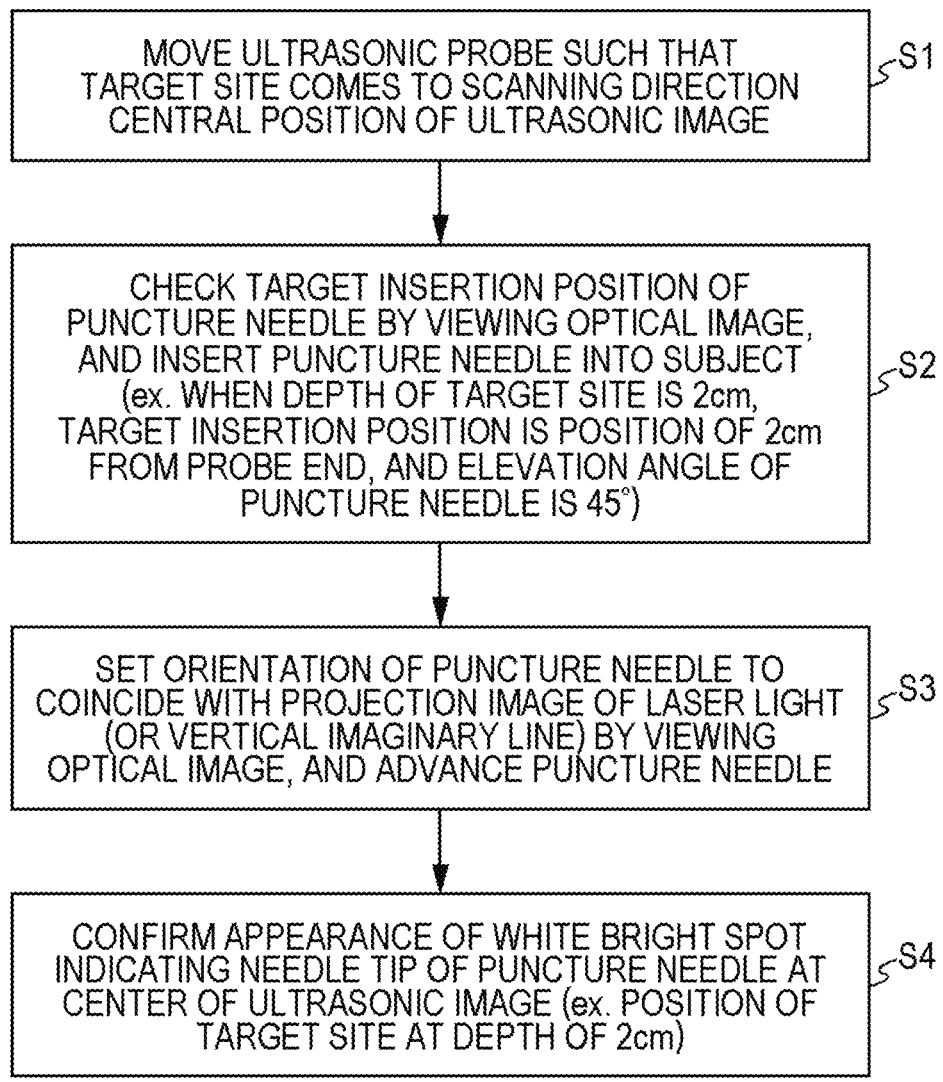
FIG. 7 is a flowchart for explaining puncture work performed by a user when the puncture needle is inserted into a body surface of a subject by using the ultrasonic diagnostic apparatus according to an embodiment of the present invention.
Figure 8:
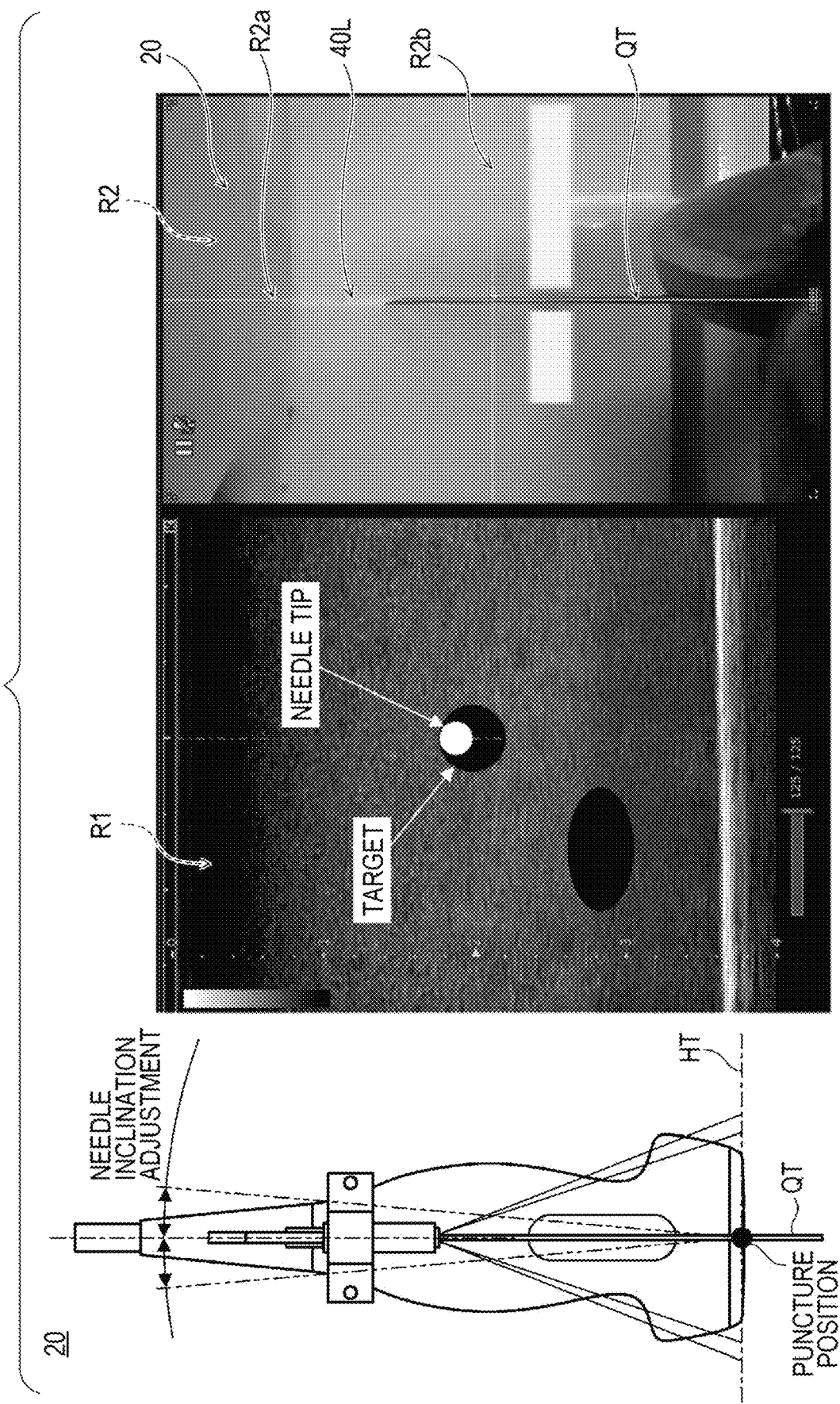
FIG. 8 is a view for explaining puncture work performed by a user when the puncture needle is inserted into a body surface of a subject by using the ultrasonic diagnostic apparatus according to an embodiment of the present invention.

FIGS. 7 and 8 are views for explaining the puncture work by the user when the puncture needle QT is inserted into the body surface of the subject HT by using the ultrasonic diagnostic apparatus 1.

Note that FIG. 7 illustrates work or operations sequentially executed by the user at the time of puncture work. The work or operations illustrated in FIG. 7 are performed in a state where the camera 30 and the laser pointer 40 are set such that a sound axis center of the ultrasonic probe 20, an optical axis of the camera 30, and an optical axis of the laser pointer 40 are aligned in front view (see FIGS. 5A and 5B). At this time, the user may check whether or not such setting has been completed by viewing the optical image R2 displayed on the display part 16 and check whether or not the vertical imaginary line R2a, the linear projection image 40L of the laser light of the laser pointer 40 formed on the body surface of the subject HT, and a marker (not illustrated) attached to the long-axis direction central position 20aa of the probe distal end part 20a are overlapped.

First, the user activates the puncture work guide mode in the ultrasonic diagnostic apparatus 1, and then moves, while viewing the ultrasonic image R1 displayed on the display part 16, the ultrasonic probe 20 such that the target site HTa to be punctured in the subject HT comes to a scanning direction central position (that is, the long-axis direction central position 20aa of the probe distal end part 20a) of the ultrasonic image R1 (step S1).

Next, by viewing the optical image R2 displayed on the display part 16, the user inserts the puncture needle QT from the body surface of the subject HT along the linear projection image 40L of the laser light of the laser pointer 40 formed on the body surface of the subject HT (step S2).

At this time, the user checks the target insertion position and the target orientation when the puncture needle QT is inserted into the body surface of the subject HT, by viewing the ultrasonic image R1 and the optical image R2 displayed on the display part 16.

For example, the target orientation of the puncture needle QT when the puncture needle QT is inserted into the body surface of the subject HT is an orientation parallel to the projection image 40L, at a position on the linear projection image 40L of the laser light in plan view.

At this time, for example, assuming that an elevation angle from the body surface of the subject HT when the puncture needle QT is inserted into the body surface of the subject HT is 45° (this angle is the most common angle as the puncture angle of the puncture needle QT), the target insertion position of the puncture needle QT is to be a position on the linear projection image 40L of the laser light. For example, when a distance of the target site HTa in the depth direction from the body surface of the subject HT is 2 cm, the target insertion position of the puncture needle QT is a position 2 cm away from the probe distal end part 20a on the body surface of the subject HT from the long-axis direction central position 20aa of the probe distal end part 20a of the ultrasonic probe 20.

At this time, for example, by using a position of the horizontal imaginary line R2b superimposed and displayed in the optical image R2 as a reference, the user may check the target insertion position of the puncture needle QT (the position 2 cm from the long-axis direction central position 20aa of the probe distal end part 20a) in the optical image R2. Further, by visually recognizing the ultrasonic image R1 and the optical image R2, the user may check the target insertion position such that a distance from the probe distal end part 20a to the target site HTa on the ultrasonic image R1 and a distance from the probe distal end part 20a to the target insertion position on the optical image R2 are the same.

Next, by viewing the optical image R2 displayed on the display part 16, the user advances the puncture needle QT into the subject HT such that an orientation (that is, an angle) of the puncture needle QT in plan view does not deviate from the projection image 40L of the laser light (or does not to deviate from the vertical imaginary line R2a) (step S3).

By the operations and work described above, the puncture needle QT reaches the position of the target site HTa in the subject HT without requiring adjustment during puncture. Then, the user confirms that a distal end of the puncture needle QT appears at the position of the target site HTa (here, the position at a depth of 2 cm from the body surface of the subject HT) in the ultrasonic image R1, and ends the puncture work (step S4). Note that the distal end of the puncture needle QT normally appears as a white bright spot in the ultrasonic image R1.

[Effect]

As described above, the ultrasonic diagnostic apparatus 1 according to the present embodiment includes:

the ultrasonic probe 20 that is arranged to allow the probe distal end part 20a to be pressed against a body surface of the subject HT, and acquires an ultrasonic image of an inside of the subject HT by transmission and reception of an ultrasonic wave;

the optical camera 30 that is attached to a proximal end side of the ultrasonic probe 20 and captures an image of an arrangement position of the probe distal end part 20a of the ultrasonic probe 20 on a body surface of the subject HT; and the laser pointer 40 that is attached to a proximal end side of the ultrasonic probe 20 and emits laser light onto the body surface of the subject HT to form the predetermined projection image 40L, to guide a target insertion position and a target orientation of the puncture needle QT when the puncture needle QT is inserted into the subject HT, in an optical image generated by the optical camera 30.

Therefore, according to the ultrasonic diagnostic apparatus 1 according to the present embodiment, it is possible to further facilitate insertion work of a puncture needle by a user into a subject. In particular, also when the user performs insertion work of the puncture needle QT into the subject HT freehand, the ultrasonic diagnostic apparatus 1 according to the present embodiment is useful in that it is possible to assist the user to be able to accurately insert the puncture needle QT into the target site HTa in the subject HT without relying on intuition.

(Modification 1)

Figure 9:
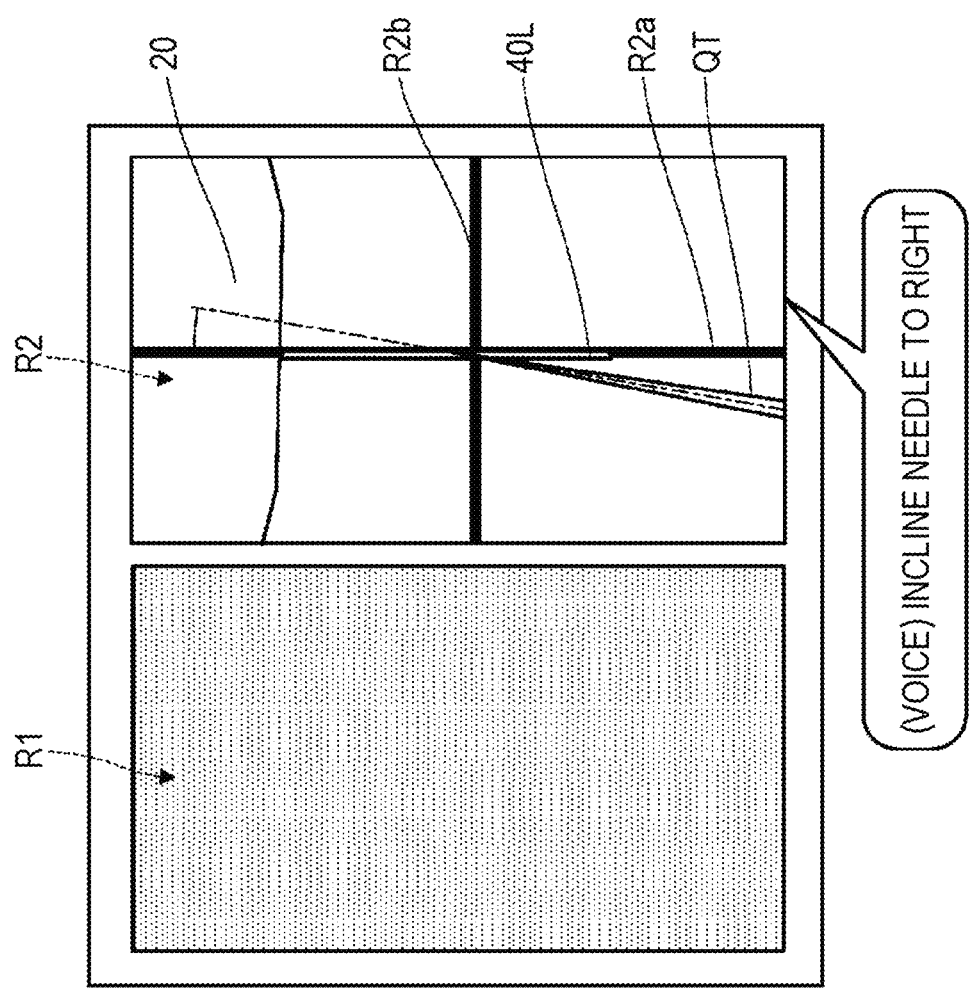
FIG. 9 is a view illustrating an example of a configuration of an ultrasonic diagnostic apparatus according to Modification 1.

FIG. 9 is a view illustrating an example of a configuration of the ultrasonic diagnostic apparatus 1 according to Modification 1. Note that FIG. 9 schematically illustrates an example of a monitor screen displayed on the display part 16 of the ultrasonic diagnostic apparatus 1 at a time of puncture work.

In the ultrasonic diagnostic apparatus 1 described in the embodiment described above, when a current orientation of the puncture needle QT deviates from a target orientation, it is more convenient for the user who is not familiar with the puncture work if an orientation correction method for correcting the puncture needle QT from the current orientation to the target orientation is performed.

In the ultrasonic diagnostic apparatus 1 according to the present modification, the control part 19 functions as such an orientation guide part. For example, the control part 19 performs image recognition processing on the optical image R2 to specify the current orientation (that is, an extending direction of the puncture needle QT in plan view) of the puncture needle QT shown in the optical image R2. Then, the control part 19 compares the current orientation of the puncture needle QT with the target orientation and specifies a deviation direction and a deviation amount, and the control part 19 specifies an orientation correction method for correcting the puncture needle QT from the current orientation to the target orientation. Note that, at this time, the control part 19 can use the extending direction of the projection image 40L of the laser light or the extending direction of the vertical imaginary line R2a in the optical image R2, as the target orientation of the puncture needle QT.

The control part 19 outputs an output command related to the orientation correction method of the puncture needle QT specified in this manner to the image composition part 15 and a speaker device (not illustrated), and thereby guides the orientation correction method to the user via voice or image display.

The method of image recognition by the control part 19 may be any method, and for example, known template matching, convolutional neural network, or the like can be used.

Note that, as an example of a guide mode of the orientation correction method for the puncture needle QT, FIG. 9 illustrates a guide mode for correcting the deviation direction of the orientation of the puncture needle QT, but guidance for correcting the deviation amount of the orientation of the puncture needle QT may be further performed.

The ultrasonic diagnostic apparatus 1 according to the present modification is useful in that an image instruction and voice guidance can be performed such that the puncture needle QT advances to a sound axis center (that is, a direction in which the target site HTa is present) of the ultrasonic probe 20. This allows the user to more easily puncture the target site HTa with the puncture needle QT.

(Modification 2)

Figure 10:
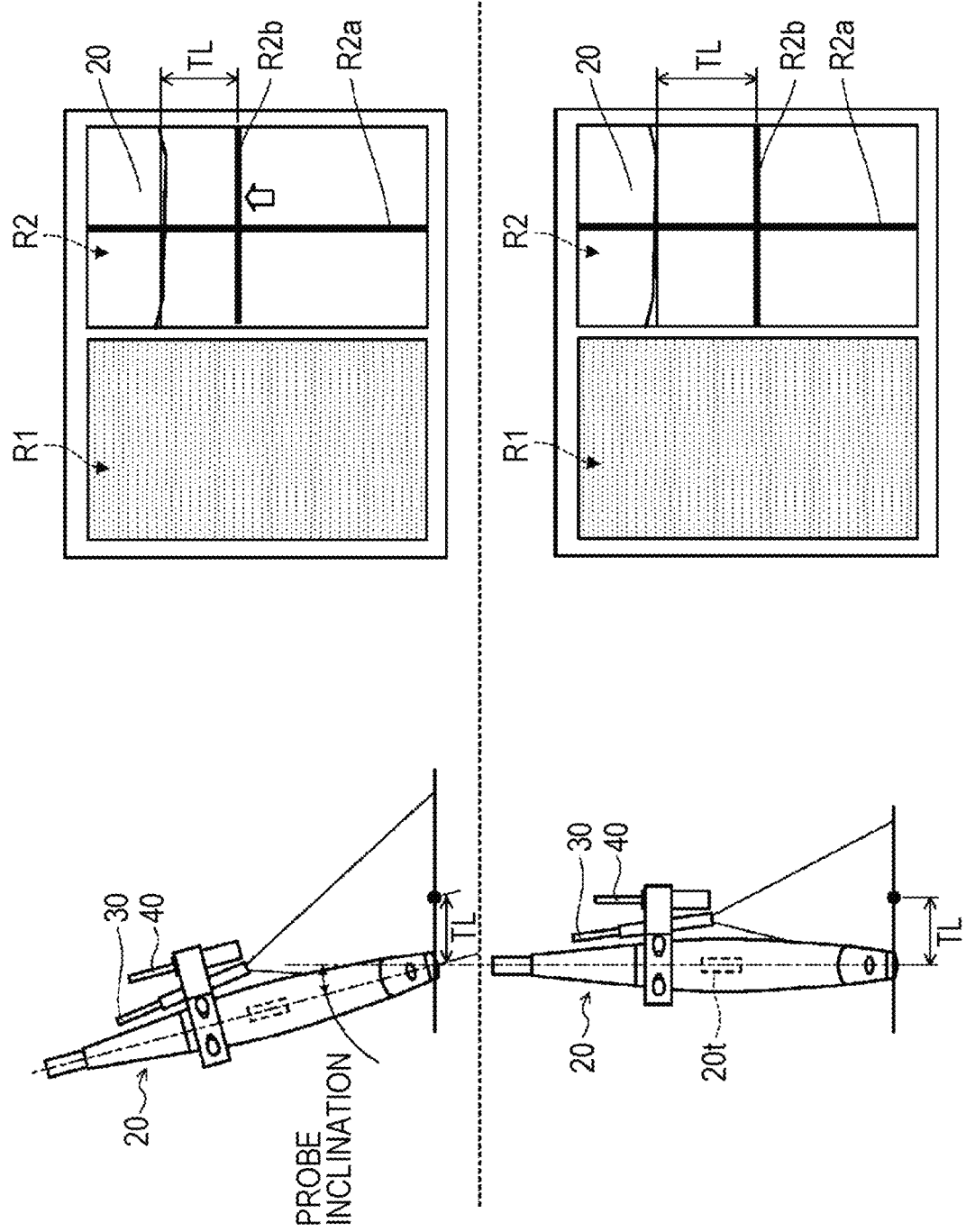
FIG. 10 is a view illustrating an example of a configuration of an ultrasonic diagnostic apparatus according to Modification 2.

FIG. 10 is a view illustrating an example of a configuration of the ultrasonic diagnostic apparatus 1 according to Modification 2. Note that a left region of FIG. 10 illustrates an orientation of the ultrasonic probe 20, and a right region of FIG. 10 illustrates an example of a monitor screen displayed on the display part 16 in accordance with the orientation of the ultrasonic probe 20. A lower part of FIG. 10 illustrates a case where an inclination angle of the ultrasonic probe 20 is 0 degrees, and an upper part of FIG. 10 illustrates a case where the inclination angle of the ultrasonic probe 20 is 20 degrees.

In the optical image R2, a distance (see TL in FIG. 10) from the probe distal end part 20a of the ultrasonic probe 20 to the target insertion position of the puncture needle QT changes in accordance with the inclination angle of the ultrasonic probe 20. Therefore, when the ultrasonic probe 20 is inclined with respect to a body surface of the subject HT, the user may erroneously recognize the distance from the probe distal end part 20a of the ultrasonic probe 20 to the target insertion position of the puncture needle QT in the optical image R2.

From such a viewpoint, in the ultrasonic diagnostic apparatus 1 according to the present modification, display of reference information of an actual distance superimposed and displayed on the optical image R2 is changed in accordance with an inclination angle of the ultrasonic probe 20 with respect to a body surface of the subject HT.

Specifically, in the ultrasonic diagnostic apparatus 1 according to the present modification, for example, the ultrasonic probe 20 is provided with an acceleration sensor 20t for detection of an inclination angle (that is, an inclination angle of the ultrasonic probe 20 with respect to a body surface of the subject HT) of the ultrasonic probe 20. Then, the image composition part 15 according to the present modification acquires a sensor signal indicating the inclination angle of the ultrasonic probe 20 from the acceleration sensor 20t, and changes a display position of the horizontal imaginary line R2b superimposed and displayed on the optical image R2 in accordance with the inclination angle of the ultrasonic probe 20.

For example, as illustrated in FIG. 10, the image composition part 15 changes the horizontal imaginary line R2b superimposed and displayed at a position 2 cm from the probe distal end part 20a in the optical image R2, in accordance with the inclination angle of the ultrasonic probe 20. A correspondence and the like between the inclination angle of the ultrasonic probe 20 and the display position of the horizontal imaginary line R2b are specified in advance and stored in a storage part (for example, the ROM 192), for example, and the image composition part 15 controls the display position of the horizontal imaginary line R2b on the basis of data indicating the correspondence.

Note that, at this time, the image composition part 15 may change the number of pieces and a line interval of the horizontal imaginary line R2b to be superimposed and displayed on the optical image R2, a scale to be superimposed and displayed on the optical image R2, or the like in accordance with the inclination angle of the ultrasonic probe 20 with respect to the body surface of the subject HT.

As described above, the ultrasonic diagnostic apparatus 1 according to the present modification is useful in that the user can accurately recognize a distance from a probe end of the ultrasonic probe 20 to a target insertion position of the puncture needle QT even when the ultrasonic probe 20 is inclined.

(Modification 3)

Figure 11:
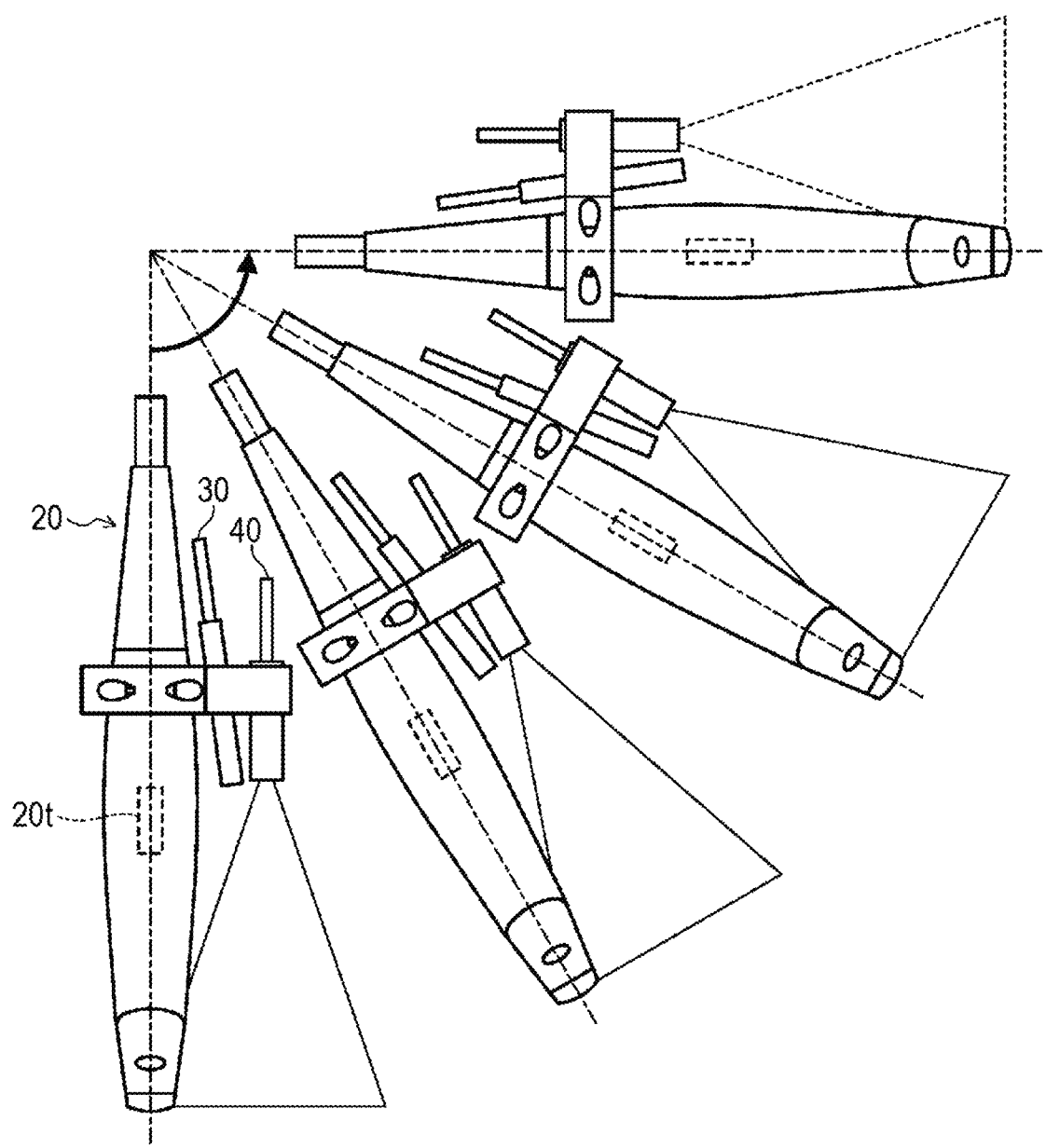
FIG. 11 is a view illustrating an example of a configuration of an ultrasonic diagnostic apparatus according to Modification 3.

FIG. 11 is a view illustrating an example of a configuration of the ultrasonic diagnostic apparatus 1 according to Modification 3. Note that FIG. 11 illustrates an example of ON/OFF of a laser light output operation by the laser pointer 40 according to an inclination of the ultrasonic probe 20 in the ultrasonic diagnostic apparatus 1 according to the present modification.

When the laser light emitted from the laser pointer 40 is incident on an eyeball of the user or the subject, there is a risk of damaging vision of the user or the subject. From such a viewpoint, in the ultrasonic diagnostic apparatus 1 according to the present modification, the output of the laser light of the laser pointer 40 can be changed according to an inclination angle of the ultrasonic probe 20.

Specifically, similarly to the ultrasonic diagnostic apparatus 1 according to Modification 2, in the ultrasonic diagnostic apparatus 1 according to the present modification, for example, the ultrasonic probe 20 is provided with the acceleration sensor 20t for detection of an inclination angle (that is, an inclination angle of the ultrasonic probe 20 with respect to a body surface of the subject HT) of the ultrasonic probe 20.

Then, the control part 19 according to the present modification acquires a sensor signal from the acceleration sensor 20t, and controls the output of the laser light of the laser pointer 40 in accordance with the detected inclination angle of the ultrasonic probe 20. Specifically, when the inclination angle of the ultrasonic probe 20 with respect to the body surface of the subject HT becomes equal to or larger than a threshold value (for example, 90 degrees), the control part 19 controls the oscillation control part 18 to interrupt the output of the laser light of the laser pointer 40.

As described above, the ultrasonic diagnostic apparatus 1 according to the present modification is useful in that it is possible to suppress a situation in which the laser light emitted from the laser pointer 40 is incident on the eyeball of the user or the subject HT.

(Modification 4)

FIG. 12 is a view illustrating an example of a configuration of the ultrasonic diagnostic apparatus 1 according to Modification 4. Note that FIG. 12 schematically illustrates an example of a monitor screen displayed on the display part 16 of the ultrasonic diagnostic apparatus 1. A lower part of FIG. 12 illustrates a state where a display scale of the ultrasonic image R1 is changed from an upper part of FIG. 12.

In the monitor screen displayed on the display part 16, it is preferable that a distance in the ultrasonic image R1 and a distance in the optical image R2 coincide with each other on the basis of an actual distance on the screen. By doing so, the user can more easily recognize the positional relationship between a position of the target site HTa on the ultrasonic image R1 and an insertion position on the optical image R2.

From such a viewpoint, in the present modification, the image composition part 15 displays the ultrasonic image R1 and the optical image R2 after controlling image sizes and the like of the ultrasonic image R1 and the optical image R2 such that display scales (that is, display magnifications) of the ultrasonic image R1 and the optical image R2 coincide with each other in the display image. That is, in the monitor screen displayed on the display part 16, the image composition part 15 matches the distance in the ultrasonic image R1 with the distance in the optical image R2 on the basis of the actual distance on the screen.

Then, the image composition part 15 according to the present modification arranges the ultrasonic image R1 and the optical image R2 side by side in a horizontal direction or a vertical direction in the display image, and displays the ultrasonic image R1 and the optical image R2 such that widths of the ultrasonic image R1 and the optical image R2 in the horizontal direction or the vertical direction coincide with each other.

In addition, when a display scale of the ultrasonic image R1 is changed (for example, when an acquisition condition of the ultrasonic image R1 in the ultrasonic probe 20 is changed), and an interval of a scale R1c of a display depth of the ultrasonic image R1 is changed, the image composition part 15 according to the present modification also changes an interval of a scale R2c to be superimposed and displayed on the optical image R2 so as to correspond to the interval of the scale R1c of the display depth of the ultrasonic image R1.

The ultrasonic diagnostic apparatus 1 according to the present modification is useful in that the user can more easily recognize a correspondence between a position of the target site HTa shown in the ultrasonic image R1 and a target insertion position of the puncture needle QT in the optical image R2.

(Modification 5)

FIG. 13 is a view illustrating an example of a configuration of the ultrasonic diagnostic apparatus 1 according to Modification 5. Note that FIG. 13 schematically illustrates an example of a monitor screen displayed on the display part 16 of the ultrasonic diagnostic apparatus 1. A lower part of FIG. 13 illustrates a state where a display size of the ultrasonic image R1 is changed from an upper part of FIG. 13.

The image composition part 15 according to the present modification can change, in the display image, from a display mode of the display image in FIG. 6 to a mode in which the ultrasonic image R1 is arranged in a lower region in the display image and the optical image R2 is arranged in an upper region in the display image, on the basis of an operation input of a user.

In addition, the image composition part 15 according to the present modification can change display sizes of the ultrasonic image R1 and the optical image R2 as illustrated in the upper part and the lower part of FIG. 13 on the basis of an operation input by the user.

As described above, the ultrasonic probe 20 according to the present modification can change a display size and/or layout of the ultrasonic image R1 and/or the optical image R2 in the display image. Therefore, the user can freely change these images to an easily viewable position and size, which is useful in that the puncture work can be more easily performed.

(Modification 6)

FIGS. 14A to 14D are views illustrating an example of a configuration of the ultrasonic diagnostic apparatus 1 according to Modification 6. Note that FIGS. 14A, 14B, 14C, and 14D individually illustrate states in which positional relationships between the ultrasonic probe 20 and the puncture needle QT are different from each other, and illustrate examples of a monitor screen displayed on the display part 16.

In general, the user checks a position of a target site while variously moving the ultrasonic probe 20 on a body surface of the subject HT. Therefore, when the user performs the puncture work, a direction of the ultrasonic probe 20 with respect to a standing position of the user is not always constant. Therefore, when the user performs the puncture work, a direction of the ultrasonic probe 20 with respect to the puncture needle QT when the user inserts the puncture needle QT varies.

From such a viewpoint, the image composition part 15 according to the present modification can vertically and horizontally reverse a direction of the optical image R2 in a display image on the basis of an operation input of the user.

FIG. 14A illustrates a display mode of the optical image R2 in a case where the puncture needle QT is present in front of the ultrasonic probe 20 with reference to the viewpoint from the user. Furthermore, FIG. 14B illustrates a display mode of the optical image R2 in a case where the puncture needle QT is present on a left side of the ultrasonic probe 20 with reference to the viewpoint from the user. Furthermore, FIG. 14C illustrates a display mode of the optical image R2 in a case where the puncture needle QT is present on a back side of the ultrasonic probe 20 with reference to the viewpoint from the user. Furthermore, FIG. 14D illustrates a display mode of the optical image R2 in a case where the puncture needle QT is present on a right side of the ultrasonic probe 20 with reference to the viewpoint from the user.

The ultrasonic probe 20 according to the present modification is useful in that a direction of the optical image R2 can be changed in accordance with an insertion direction of the puncture needle QT, and the user can intuitively recognize the insertion mode of the puncture needle QT.

(Modification 7)

Figure 15:
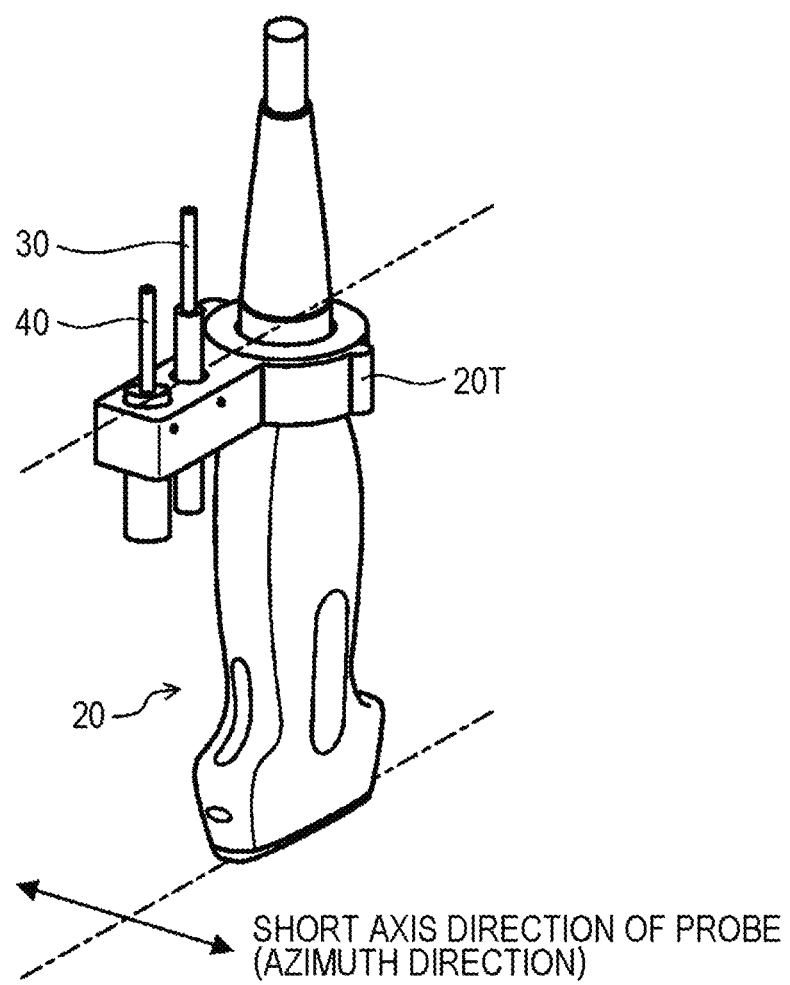
FIG. 15 is a view illustrating an example of a configuration of an ultrasonic diagnostic apparatus according to Modification 7.

FIG. 15 is a view illustrating an example of a configuration of the ultrasonic diagnostic apparatus 1 according to Modification 7. FIG. 15 illustrates an example of a configuration of the attachment 20T attached to the ultrasonic probe 20.

Figure 17:
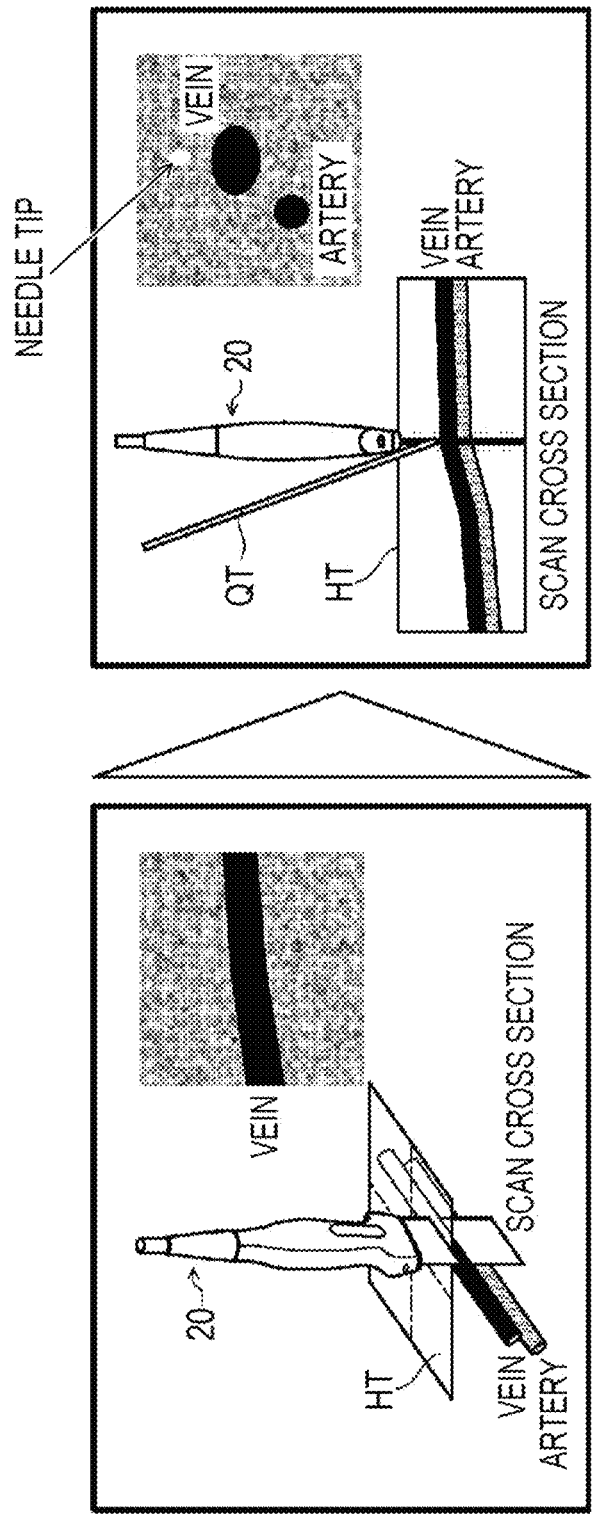
FIG. 17 illustrates a way of pressing an ultrasonic probe against a body surface of a subject in each of a parallel method (a left part of FIG. 17) and a cross method (a right part of FIG. 17).

The embodiment described above has shown an example of an attachment state of the camera 30 and the laser pointer 40 in the attachment 20T on the assumption that puncture work on a blood vessel is performed by a cross method (a right part of FIG. 17) under the guide in the ultrasonic diagnostic apparatus 1. However, the ultrasonic diagnostic apparatus 1 (that is, the attachment 20T) according to the present disclosure can also assist puncture work when the puncture needle QT is inserted into a subject in various orientations without limiting to when the puncture needle QT is inserted into the subject by the cross method.

FIG. 15 illustrates a configuration of the attachment 20T that is useful when puncture work of a blood vessel is performed by a parallel method under the guide in the ultrasonic diagnostic apparatus 1. In the attachment 20T according to the present modification, the camera 30 and the laser pointer 40 are set such that a center position of the ultrasonic probe 20 in a short axis direction, an optical axis of the camera 30, and an optical axis of the laser pointer 40 coincide with each other in side view.

That is, the projection image 40L formed by the laser light of the laser pointer 40 presents a linear shape extending from a starting point toward a direction orthogonal to the short axis direction (that is, a direction away from the probe distal end part 20a), for example, on a body surface of the subject HT, with a central position of the probe distal end part 20a of the ultrasonic probe 20 in the short axis direction as the starting point. Also in this aspect, by using, as a reference, a position of the probe distal end part 20a of the ultrasonic probe 20 arranged on the body surface of the subject HT, it is possible to guide a position of a target site (for example, a blood vessel to be punctured) shown in the ultrasonic image R1, and further, the target orientation and the target insertion position of the puncture needle QT when the puncture needle QT is inserted into the subject HT.

(Modification 8)

Figure 16:
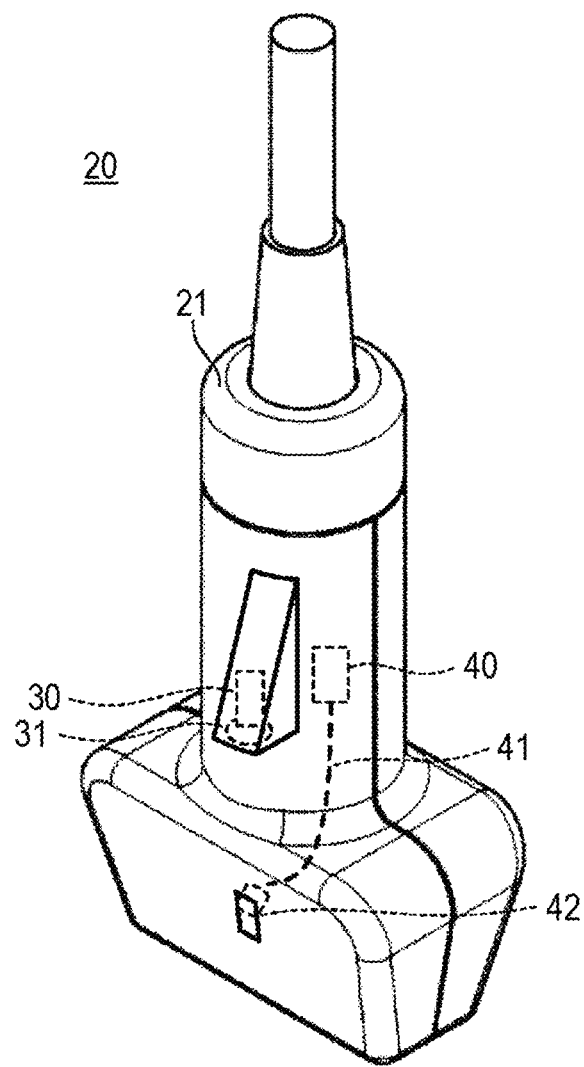
FIG. 16 is a view illustrating an example of a configuration of an ultrasonic diagnostic apparatus according to Modification 8.

FIG. 16 is a view illustrating an example of a configuration of the ultrasonic diagnostic apparatus 1 according to Modification 8. FIG. 16 illustrates an example of a configuration of the ultrasonic probe 20.

In the embodiment described above, an aspect has been shown in which the camera 30 and the laser pointer 40 are prepared separately from the housing 21 of the ultrasonic probe 20, and are attached to the housing 21 of the ultrasonic probe 20 via the attachment 20T. However, the camera 30 and the laser pointer 40 may be incorporated in the housing 21 of the ultrasonic probe 20.

FIG. 16 illustrates an example of an aspect in which the camera 30 and the laser pointer 40 are incorporated in the housing 21 of the ultrasonic probe 20.

In the ultrasonic probe 20 according to the present modification, the housing 21 is used in which the camera 30 and the laser pointer 40 are incorporated in the housing 21, and an optical fiber 41 that guides the laser light emitted from the laser pointer 40, a window 42 for emission of the laser light emitted by the laser pointer 40, and an image-capturing window 31 of the camera 30, and the like are provided.

The ultrasonic probe 20 according to the present modification is useful in that damage or the like of the camera 30 and the laser pointer 40 can be inhibited.

According to the ultrasonic diagnostic apparatus according to the present disclosure, it is possible to further facilitate insertion work of a puncture needle by a user into a living body.

Although embodiments of the present invention have been described and illustrated in detail, the disclosed embodiments are made for purposes of illustration and example only and not limitation. The scope of the present invention should be interpreted by terms of the appended claims. The technology described in the claims includes various modifications and changes of the specific examples exemplified above.

What is claimed is:

1. An ultrasonic diagnostic apparatus for assisting insertion work of a puncture needle into a subject, the ultrasonic diagnostic apparatus comprising:
   an ultrasonic probe that is arranged to allow a probe distal end part to be pressed against a body surface of the subject, and configured to acquire an ultrasonic image of an inside of the subject by transmission and reception of an ultrasonic wave;
   a laser pointer that is attached to a proximal end side of the ultrasonic probe and configured to emit laser light onto the body surface of the subject to form a predetermined projection image; and
   an optical camera that is attached to the proximal end side of the ultrasonic probe and configured to capture an optical image in a plane orthogonal to a sound axis center of the ultrasonic probe, the optical image including an arrangement position of the probe distal end part of the ultrasonic probe, the body surface of the subject and the predetermined projection image formed by the laser light,
   wherein the predetermined projection image is configured to guide a target insertion position and a target orientation of the puncture needle when the puncture needle is inserted into the subject, in the optical image acquired by the optical camera.

2. The ultrasonic diagnostic apparatus according to claim 1, wherein
   the predetermined projection image formed by the laser light is configured to guide the target insertion position and the target orientation of the puncture needle with the probe distal end part of the ultrasonic probe as a reference position, in the optical image acquired by the optical camera.

3. The ultrasonic diagnostic apparatus according to claim 1, wherein
   the predetermined projection image formed by the laser light has a linear shape extending in a direction orthogonal to a long axis direction with, as a starting point, a central position in the long axis direction of the probe distal end part of the ultrasonic probe.

4. The ultrasonic diagnostic apparatus according to claim 1, wherein
   an optical axis of the optical camera and the sound axis center of the ultrasonic probe overlap with a center axis of the predetermined projection image of the laser light outputted from the laser pointer, when the predetermined projection image is projected onto the body surface of the subject.

5. The ultrasonic diagnostic apparatus according to claim 1, wherein
   the optical camera is attached to the ultrasonic probe to show, in the optical image, the probe distal end part of the ultrasonic probe, the predetermined projection image of the laser light projected on the body surface of the subject, and an observation target site of the ultrasonic image on the body surface of the subject.

6. The ultrasonic diagnostic apparatus according to claim 1, wherein
   the optical camera and the laser pointer are attached to a housing of the ultrasonic probe via a detachable attachment.

7. The ultrasonic diagnostic apparatus according to claim 1, further comprising:
an image composition part that is configured to acquire the ultrasonic image from the ultrasonic probe, acquire the optical image from the optical camera, and generate a display image to display the optical image and the ultrasonic image in a same monitor screen.

8. The ultrasonic diagnostic apparatus according to claim 7, wherein
the image composition part is configured to match display scales of the ultrasonic image and the optical image with each other in the display image, and arrange the ultrasonic image and the optical image side by side in a horizontal direction or a vertical direction.

9. The ultrasonic diagnostic apparatus according to claim 7, wherein
the image composition part is configured to superimpose and display a vertical imaginary line indicating a line corresponding to an optical axis of the optical camera and a horizontal imaginary line indicating a line orthogonal to the optical axis of the optical camera, in the optical image.

10. The ultrasonic diagnostic apparatus according to claim 9, wherein
the image composition part is configured to change a number of pieces and a line interval of the horizontal imaginary line and/or a scale interval to be given to the vertical imaginary line in accordance with an inclination angle of the ultrasonic probe with respect to the body surface of the subject.

11. The ultrasonic diagnostic apparatus according to claim 7, wherein
the image composition part is configured to change a scale interval to be displayed in the optical image in accordance with a scale interval of a display depth of the ultrasonic image.

12. The ultrasonic diagnostic apparatus according to claim 7, wherein
the image composition part is capable of vertically and horizontally reversing a direction of the optical image in the display image, based on an operation input by a user.

13. The ultrasonic diagnostic apparatus according to claim 7, wherein
the image composition part is capable of changing a display size and/or a layout of the ultrasonic image and/or the optical image in the display image, based on an operation input by a user.

14. The ultrasonic diagnostic apparatus according to claim 1, further comprising:
a hardware processor that is configured to specify a current orientation of the puncture needle by performing image analysis on the optical image, and guide, to a user, a correction mode for bringing the puncture needle closer to the target orientation from the current orientation.

15. The ultrasonic diagnostic apparatus according to claim 1, wherein
the laser pointer is controlled to interrupt emission of the laser light when an inclination angle of the ultrasonic probe with respect to the body surface of the subject becomes equal to or larger than a threshold value.

16. An ultrasonic probe for assisting insertion work of a puncture needle into a subject, the ultrasonic probe comprising a housing, a laser pointer and an optical camera, the laser pointer and the optical camera being incorporated in the housing,
wherein the ultrasonic probe is arranged to allow a probe distal end part to be pressed against a body surface of the subject, and configured to acquire an ultrasonic image of an inside of the subject by transmission and reception of an ultrasonic wave,
the laser pointer is configured to emit laser light onto the body surface of the subject to form a predetermined projection image,
the optical camera is configured to capture an optical image in a plane orthogonal to a sound axis center of the ultrasonic probe, the optical image including an arrangement position of the probe distal end part of the ultrasonic probe, the body surface of the subject and the predetermined projection image formed by the laser light, and
the predetermined projection image is configured to guide a target insertion position and a target orientation of the puncture needle when the puncture needle is inserted into the subject, in the optical image acquired by the optical camera.

* * * * *